United States Patent
Krichevsky et al.

(10) Patent No.: US 9,150,928 B2
(45) Date of Patent: Oct. 6, 2015

(54) DIAGNOSING AND MONITORING CNS MALIGNANCIES USING MICRORNA

(75) Inventors: Anna M. Krichevsky, Brookline, MA (US); Nadiya Teplyuk, Boston, MA (US); Brit Mollenhauer, Kassel (DE); Santosh Kesari, San Diego, CA (US)

(73) Assignees: The Brigham and Women's Hospital, Inc., Boston, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/885,762

(22) PCT Filed: Nov. 16, 2011

(86) PCT No.: PCT/US2011/061047
§ 371 (c)(1),
(2), (4) Date: Sep. 3, 2013

(87) PCT Pub. No.: WO2012/068288
PCT Pub. Date: May 24, 2012

(65) Prior Publication Data
US 2013/0344063 A1 Dec. 26, 2013

Related U.S. Application Data

(60) Provisional application No. 61/457,000, filed on Nov. 16, 2010.

(51) Int. Cl.
*C12Q 1/68* (2006.01)
*G06F 19/18* (2011.01)
*G06F 19/24* (2011.01)

(52) U.S. Cl.
CPC .............. *C12Q 1/6886* (2013.01); *G06F 19/18* (2013.01); *C12Q 2600/118* (2013.01); *C12Q 2600/178* (2013.01); *G06F 19/24* (2013.01)

(58) Field of Classification Search
None
See application file for complete search history.

(56) References Cited

U.S. PATENT DOCUMENTS

2006/0105360 A1 5/2006 Croce et al.
2010/0167948 A1 7/2010 Krichevsky et al.
2010/0178653 A1 7/2010 Aharonov et al.

FOREIGN PATENT DOCUMENTS

WO WO-2008153692 A2 * 12/2008

OTHER PUBLICATIONS

Lu et al (Nature 435: 834 (2005)).*
Baffa et al., "MicroRNA expression profiling of human metastatic cancers identifies cancer gene targets," J. Pathol., 219(2):214-221 (2009).
Baraniskin et al., "Identification of microRNAs in the cerebrospinal fluid as biomarker for the diagnosis of glioma," Neuro. Oncol., 14(1):29-33 (2012; Advance Access publication Sep. 21, 2011).
Baraniskin et al., "Identification of microRNAs in the cerebrospinal fluid as markers for primary diffuse large B-cell lymphoma of the central nervous system," Blood, 117:3140-3146 (2011).
Birks et al., "Survey of MicroRNA expression in pediatric brain tumors," Pediatr. Blood Cancer, 56(2):211-216 (2011).
Chan et al., "MicroRNA-21 is an antiapoptotic factor in human glioblastoma cells," Cancer Res., 65(14):6029-6033 (2005).
Chen et al., Characterization of microRNAs in serum: a novel class of biomarkers for diagnosis of cancer and other diseases. Cell Res., 18(10):997-1006 (2008).
Cogswell et al., "Identification of miRNA changes in Alzheimer's Disease Brain and CSF Yields Putative Biomarkers and Insights into Disease Pathways," Journal of Alzheimer's Disease, 14:27-41 (2008).
Filippini et al., "Prognostic factors for survival in 676 consecutive patients with newly diagnosed primary glioblastoma," Neuro Oncol., 10(1):79-87 (2008).
Gabriely et al., "Human glioma growth is controlled by microRNA-10b," Cancer Res., 71(10):3563-3572 (2011).
Gabriely et al., "MicroRNA 21 promotes glioma invasion by targeting matrix metalloproteinase regulators," Mol. Cell Biol., 28(17):5369-5380 (2008).
Gaur et al., "Downregulation of Pdcd4 by mir-21 facilitates glioblastoma proliferation in vivo," Neuro Oncol.13(6):580-590 (2011).
Gilad et al., "Serum microRNAs are promising novel biomarkers," PLoS One, 3(9):e3148 (2008).
Heneghan et al., "Systemic miRNA-195 differentiates breast cancer from other malignancies and is a potential biomarker for detecting noninvasive and early stage disease," Oncologist. 15(7):673-682 (2010).
Hudson et al., "International network of cancer genome projects," Nature, 464:993-998 (2010).
International Search Report issued in PCT/US2011/061047 on Jul. 9, 2012.
Jackman et al., "Response and resistance in a non-small-cell lung cancer patient with an epidermal growth factor receptor mutation and leptomeningeal metastases treated with high-dose gefitinib," J. Clin. Oncol., 24(27):4517-4520 (2006).
Keller et al., "miRNAs in lung cancer—studying complex fingerprints in patient's blood cells by micro array experiments," BMC Cancer, 9:353 (2009).
Korpal et al., "The emerging role of miR-200 family of microRNAs in epithelial-mesenchymal transition and cancer metastasis," RNA Biol., 5(3):115-119 (2008).
Krichevsky et al., "miR-21: a small multi-faceted RNA," J. Cell Mol. Med., 13(1):39-53 (2009).
Lawrie et al., "Detection of elevated levels of tumour-associated microRNAs in serum of patients with diffuse large B-cell lymphoma," Br. J. Haematol., 141(5):672-675 (2008).
Liang et al., "Characterization of micro RNA expression profiles in normal human tissues," BMC Genomics, 8:166 (2007).
Lu et al., "MicroRNA expression profiles classify human cancers," Nature, 435(7043):834-838 (2005).
Ma et al., "Tumour invasion and metastasis initiated by microRNA-10b in breast cancer," Nature, 449(7163):682-688 (2007).

(Continued)

*Primary Examiner* — James Martinell
(74) *Attorney, Agent, or Firm* — Fish & Richardson P.C.

(57) ABSTRACT

The use of specific microRNAs (miRNAs) present in CSF as biomarkers for particular brain malignancies and disease activity.

11 Claims, 24 Drawing Sheets

(56) References Cited

OTHER PUBLICATIONS

Mitchell et al., "Circulating microRNAs as stable blood-based markers for cancer detection," Proc. Natl. Acad. Sci. USA, 105(30):10513-10518 (2008).

Murakami et al., "Comprehensive analysis of micro RNA expression patterns in hepatocellular carcinoma and non-tumorous tissues," Oncogene, 25(17):2537-2545 (2006).

Nass et al., "MiR-92b and miR-9/9 are specifically expressed in brain primary tumors and can be used to differentiate primary from metastatic brain tumors," Brain Pathol., 19(3):375-383 (2009).

Network CGAR, "Comprehensive genomic characterization defines human glioblastoma genes and core pathways," Nature, 455(7216):1061-1068 (2008).

Sasayama et al., "MicroRNA-10b is overexpressed in malignant glioma and associated with tumor invasive factors, uPAR and RhoC," Int. J. Cancer., 125(6):1407-1413 (2009).

Schramedei et al., "MicroRNA-21 targets tumor 25 suppressor genes ANP32A and SMARCA4," Oncogene, 30(26):2975-2985 (2011).

Skog et al., "Glioblastoma microvesicles transport RNA and proteins that promote tumour growth and provide diagnostic biomarkers," Nat. Cell. Biol., 10(12):1470-1476 (2008).

Volinia et al., "A microRNA expression signature of human solid tumors defines cancer gene targets," Proc. Natl. Acad. Sci. USA, 103(7):2257-2261 (2006).

Weber et al., "The MicroRNA Spectrum in 12 Body Fluids," Clinical Chemistry, 56:1733-1741 (2010).

Zhang et al., "Expression profile of microRNAs in serum: a fingerprint for esophageal squamous cell carcinoma," Clin. Chem., 56(12):1871-1879 (2010).

Zhang et al., "Profiling alternatively spliced mRNA isoforms for prostate cancer classification," BMC Bioinformatics, 7:202 (2006).

* cited by examiner

DIAGNOSING AND MONITORING CNS MALIGNANCIES USING MICRORNA

FEDERALLY SPONSORED RESEARCH OR DEVELOPMENT

This invention was made with Government support under Grant Nos. CA023100, CA124804, and CA138734 awarded by the National Institutes of Health. The Government has certain rights in the invention.

CLAIM OF PRIORITY

This application is a U.S. National Phase Application under 35 U.S.C. 371 of International Patent Application No. PCT/US2011/061047, filed on Nov. 16, 2011, which claims the benefit of U.S. Provisional Patent Application Ser. No. 61/457,000, filed on Nov. 16, 2010. The entire contents of the foregoing are hereby incorporated by reference in their entireties.

TECHNICAL FIELD

The present methods relate to the use of specific microRNAs (miRNAs) that are present in CSF as biomarkers for particular brain malignancies and disease activity.

BACKGROUND

The most frequently occurring brain malignancies in adults are metastatic brain cancers (e.g., from primary melanoma, lung cancer, breast cancer, gastrointestinal cancer (e.g., pancreatic or colorectal), kidney cancer, bladder cancer, certain sarcomas, or testicular or germ cell tumors) followed by glioblastoma (GBM). GBM is the most aggressive primary brain cancer, which generally has a poor prognosis with median survival of about 14 months, despite aggressive treatment (Filippini et al. Neuro Oncol. 2008; 10(1):79-87). Currently diagnosis of brain tumors is made with brain biopsy if possible and the analysis of cerebrospinal fluid (CSF) for the presence of cancer cells (cytology). CSF can be accessed readily for longitudinal disease monitoring during and after therapy. However, the currently used method of CSF analysis has moderate sensitivity, is non-quantitative and technically challenging. There is presently no routine way to subtype the malignancy and monitor molecular changes from CSF indicating the need for more accurate and reliable biomarkers and methods.

SUMMARY

The present invention is based on the identification of specific miRNAs that can serve as biomarkers for particular brain malignancies and disease activity.

Thus, in a first aspect, the invention provides methods for detecting or making a diagnosis between metastatic and primary brain tumors. The methods include determining levels of miR-10b, miR-21, and miR-200 in a sample from a subject, and comparing the levels of miR-10b, miR-21, and miR-200 to reference levels of miR-10b, miR-21, and at least one miR-200 family member. The presence of levels of all of miR200, miR-10b or miR-21 below the reference levels indicates the absence of a metastatic or primary brain tumor. The presence of levels of miR-10b or miR-21 above the reference levels indicates the presence of a metastatic or primary brain tumor. The presence of levels of the miR-200 family member above the reference level indicates the presence of a metastatic brain tumor.

In another aspect, the invention provides computer-implemented methods for detecting or making a diagnosis between metastatic and primary brain tumors. The methods include determining levels of miR-10b, miR-21, and at least one miR-200 family member, in a sample from a subject, to provide a subject dataset; downloading the dataset into a computer system having a memory, an output device, and a processor programmed for executing an algorithm, wherein the algorithm assigns the datasets into one of two categories levels of miR-10b, miR-21, and at least one miR-200 family member; assigning the subject dataset into the first or second category; and generating an output comprising a report indicating the assignment to the first or second category.

In some embodiments, the first category is presence of a primary brain tumor and the second category is presence of a metastatic brain tumor. In some embodiments, an assignment to the first category is made based on the presence of levels of miR-10b or miR-21 above reference levels, and the presence of levels of the miR-200 family member below a reference level; and an assignment to the second category is made based on the presence of levels of miR-10b or miR-21 above reference levels, and the presence of levels of the miR-200 family member above the reference level.

In some embodiments, the first category is presence of a primary brain tumor or a metastatic brain tumor, and the second category is absence of a primary brain tumor or a metastatic brain tumor. In some embodiments, an assignment to the first category is made based on the presence of any of miR200, miR-10b or miR-21 above reference levels, and an assignment to the second category is made based on the presence of levels of all of miR200, miR-10b or miR-21 below the reference levels.

In some embodiments, the algorithm is a linear algorithm or radial basis function.

In some embodiments, the algorithm is a linear algorithm comprising:

(a*miR-125b)+(b*miR-10b)+(c*miR-21)+(d*miR-141)+(e*miR-200a)+(f*miR-200b)+(g*miR-200c)−h, wherein a-g are weights and h is a constant, determined using a support vector machine algorithm.

In some embodiments, the methods further include selecting a treatment for a metastatic or primary brain tumor for the subject, based on the presence of a metastatic or primary brain tumor.

In some embodiments, the methods further include administering the treatment to the subject.

In another aspect, the invention provides methods for monitoring progression of a brain tumor. The methods include determining levels of one or more of miR-10b, miR-21, and a miR-200 family member in a first sample; and determining levels of one or more of miR-10b, miR-21, and a miR-200 family member in a subsequent sample. The presence of levels of miR-10b, miR-21, or miR-200 family member in the subsequence sample above the levels in the first sample indicates the presence of progression or recurrence of the brain tumor, and levels of miR-10b miR-21, or miR-200 family member in the subsequent sample below the levels in the first sample indicates that the brain tumor is regressing or is in remission.

In some embodiments, wherein the subject has been diagnosed with a primary brain tumor, the methods include monitoring levels of one or both of miR-10b and miR-21. In some embodiments, wherein the subject has been diagnosed with a metastatic brain tumor, the methods include monitoring levels of one or more of miR-10b, miR-21, and a miR-200 family member.

In some embodiments, the methods further include administering a treatment to the subject, e.g., between the first and subsequent samples, and a decrease in levels of miR-10b, miR-21, or at least one miR-200 family member in the subsequence sample as compared to the level in the first sample indicates that the treatment was effective, e.g., reduced the size of the tumor. No change indicates that the treatment either halted tumor growth or had no effect, and an increase indicates that the treatment was not effective.

In some embodiments, the treatment includes administration of one or more of surgical resection, chemotherapy, or radiotherapy.

In some embodiments of the methods described herein, the sample comprises cerebrospinal fluid from a subject.

In some embodiments of the methods described herein, the subject is a human who has or is suspected of having a brain tumor.

In some embodiments of the methods described herein, the levels are determined using RT-PCR.

In some embodiments of the methods described herein, the miR-200 family member is miR-200a, miR-200b, miR-200c, miR-141, or miR-429.

In some embodiments of the methods described herein, the method comprises normalizing the levels to a level of a housekeeping miRNA, e.g., miR-125 or miR-24.

In some embodiments of the methods described herein, the primary brain tumor is a glioma, glioblastoma, hemangioma, or medulloblastoma.

In some embodiments of the methods described herein, the metastatic brain tumor is from a primary lung, breast, kidney, bladder, testicular, germ cell or gastrointestinal cancer, or melanoma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2 C-F. (2F) The average levels of miR-200a/miR-200b and miR-141/miR-200c cluster miRNAs in CSF of metastatic brain cancer patients. The error bars represent the standard error of mean for each group of patients.

Figure 1A:
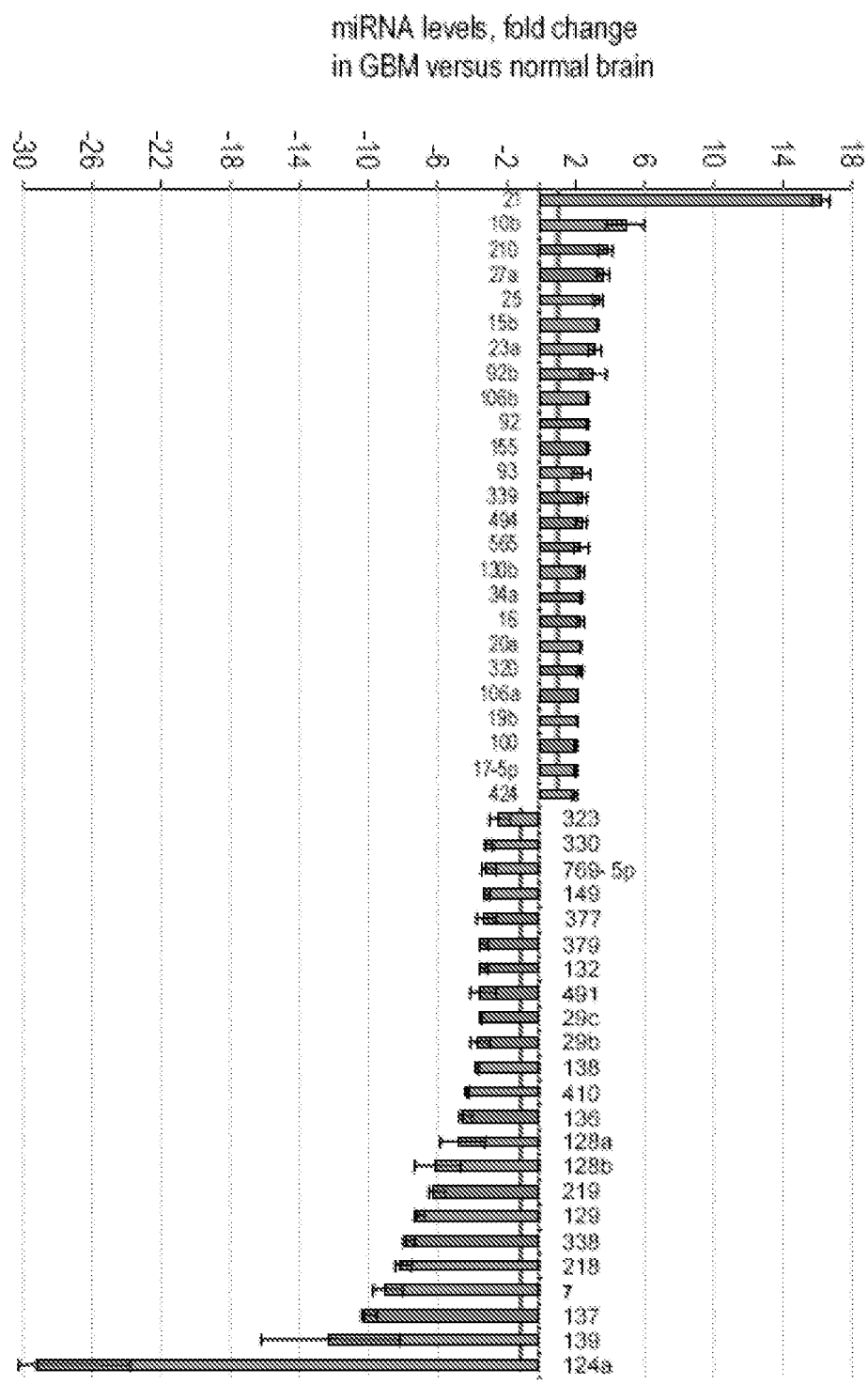
FIGS. 1A-C show miR-10b and miR-21 up-regulation in GBM, and CSF levels of miR-10b and miR-21 in patients with GBM, metastatic brain cancer and non-neoplastic controls. (1A) miRNAs deregulated in GBM more than two fold as compared to normal brains. miRNA levels were obtained by the analysis of TCGA miRNA microarrays data and error bars represent standard deviation between individual probe sets present for each miRNA on the arrays. (1B) miR-10b and (1C) miR-21 levels were examined by qRT-PCR in CSF samples of neurological patients, and the relative levels are demonstrated for individual CSF samples. The lines indicate median miRNA levels for each group of patients: "Controls"—non-neoplastic neuropathological cases, "GBM"—glioblastoma cases, "Breast to Brain" and "Lung to Brain"—breast and lung cancer brain metastasis, "Breast LM" and "Lung LM"—breast and lung cancer leptomeningeal metastasis, respectively. Differences between group means have been determined by non-parametric Wilcoxon Signed Rank test and the significance is indicated by asterisks: (*) $p<0.05$, () $p<0.001$, (*) $p<0.0001$. miR-10b and miR-21 CSF levels normalized to miR-125b are presented in FIGS. 6A-B.

DETAILED DESCRIPTION miRNAs are small endogenous mediators of RNA interference and key regulatory components of many biological processes required for organism development, cell specialization and homeostasis. Many miRNAs exhibit tissue-specific patterns of expression and are deregulated in various cancers, where they can either be oncogenic (oncomirs) or tumor suppressive. The recent discovery of miRNAs in the secreted membrane vesicles, exosomes[2,3], as well as in the blood serum[4,5] and other body fluids[6] suggested that miRNAs play a role in intercellular communication in both paracrine and endocrine manner. It had also opened a new exciting direction for study of miRNAs as biomarkers for diseases, and cancer diagnostics by miRNA profile in blood serum became a quickly growing field[7].

Several studies have reported miRNA detection, among several biological fluids, in CSF[8-10], raising the possibility that miRNAs in CSF might serve as informative biomarkers of central nervous system (CNS) disease. Such a possibility, largely unexplored until now, is supported by the finding that different types of brain cancer have distinct signatures of miRNA expression, with some miRNAs species abundant in cancer while undetectable in healthy brain[11-13]. Since CSF is separated from blood circulation by blood-brain barrier, it is conceivable that CSF might better retain a unique signature of miRNA expression specific for brain tumors.

A recent study demonstrated the usefulness of miRNA profiling in CSF for diagnostics of brain lymphoma[10]. In the current study, levels of several candidate miRNAs were tested in the CSF of patients with GBM and compared to those of metastatic brain cancers and a variety of non-neoplastic CNS diseases. There was a strong association between the particular types of brain cancer and the presence of specific miRNAs in CSF. Using this approach enables detection of GBM and metastatic brain cancers, and discrimination between them with about 95% accuracy. These results demonstrate the utility of miRNA as biomarkers of high-grade brain malignancies and reveal their value for the development of diagnostic and prognostic tools, as well as for monitoring of CNS pathology in general.

Methods of Diagnosis/Detection of CNS Malignancies

Thus, the methods described herein can be used to diagnose, i.e., detect the presence of, a CNS malignancy, based on levels of miRNAs in CSF, e.g., levels of one or more of miR-21, miR-10b, and or a miR-200 (as used herein, the term "miR-200" encompasses all members of the miR-200 family, i.e., miR-200a, miR-200b, miR-200c, miR-141, and miR-429). In some embodiments, levels of miR-110b are determined and compared to a reference level, and the presence of levels of miR-10b in the subject above the reference level indicates that the subject has a metastatic or neoplastic primary brain tumor, e.g., GBM. In some embodiments, levels of miR-200 are determined and compared to a reference level, and the presence of levels of miR-200 (e.g., miR-200a) in the subject above the reference level indicates that the subject has a metastatic brain tumor, e.g., from primary lung or breast cancer. In some embodiments, levels of miR-21 are determined and compared to a reference level, and the presence of levels of miR-21 in the subject above the reference level indicates that the subject has a metastatic or neoplastic primary brain tumor, e.g., GBM. In some embodiments, the methods include determining levels of miR-10b or miR-21 and miR-200 (either non-normalized or normalized to relatively uniformly expressed miRNAs such as miR-125 or miR-24), and comparing the levels of each miRNA to a reference level. In this case, the presence of elevated miR-10b or miR-21 indicates the presence of a metastatic or neoplastic primary brain tumor, e.g., GBM, and the presence of miR-200 indicates the presence of a metastatic brain tumor. See, e.g., FIG. 3A.

In some embodiments, the methods are used to determine whether a metastatic brain tumor originated from a primary breast or lung tumor. The methods include detecting levels of miR-200a and/or miR-200b. The presence of increased levels of miR-200a and miR-200b (two miRNAs encoded as a cluster at chromosome 1p36.33) in CSF indicate an increased likelihood of the presence of metastatic breast cancer relative to lung cancer. In some embodiments, the methods include determining CSF levels of miR-141 and -200c (co-encoded at chromosome 12p13.31), which are expressed at similar levels in breast and lung cancer cases, and determining a ratio between the miRNAs of the two different miR-200 genomic clusters (e.g., [level of miR200a+level of miR200b]/[level of miR141+miR200c], wherein a ratio above a reference ratio indicates an increased likelihood of the presence of metastatic breast cancer relative to lung cancer.

In some embodiments, the methods are used to make a differential diagnosis of GBM versus brain metastasis, or GBM and brain metastasis versus non-neoplastic tumors on the basis of detection of levels in a CSF sample of seven miRNAs: miR-10b, miR-21, miR-125b, miR-141, miR-200a, miR-200b, and miR-200c as independent variables. Each of these miRNAs is detected in the sample, and an algorithm (e.g., a linear or radial is applied to make a diagnosis.

Reference levels can be determined using methods known in the art, e.g., standard epidemiological and biostatistical methods. The reference level can represent the levels in a reference cohort, e.g., levels in subjects who do not have GBM or metastatic brain cancer. The reference levels can be, e.g., median levels, or levels representing a cutoff for the highest quartile, and can be set to provide sufficient specificity and accuracy to provide for an optimal level of true positives/true negatives while minimizing levels of false positives/false negatives. Appropriate methods are known in the art. See, e.g., Fleiss, "Design and Analysis of Clinical Experiments," (Wiley-Interscience; 1 edition (Feb. 22, 1999)); Lu and Fang, "Advanced Medical Statistics," (World Scientific Pub Co Inc (Mar. 14, 2003)); Armitage et al., "Statistical Methods in Medical Research, $4^{th}$ Ed", Blackwell Science (Boston, Mass., Oxford: Blackwell Scientific Publications, 2001).

In some embodiments, the methods include determining levels of miR-125b, and normalizing levels of other miRNAs to the levels of miR-125b, see, e.g., FIGS. 5A-5G. The reference levels can then be set in comparison to those normalized levels, using methods known in the art.

In some embodiments, miRNA levels are determined after an initial diagnosis of a brain mass, e.g., detection of a mass using an imaging method such as MRI, or after a subject has presented with symptoms that are consistent with a brain mass, to assist in making a differential diagnosis of GBM versus brain metastasis versus non-neoplastic tumor. A health care provider can identify subjects who have symptoms consistent with a brain mass based on knowledge in the art; general signs and symptoms include new onset or change in pattern of headaches; headaches that gradually become more frequent and more severe; unexplained nausea or vomiting; vision problems, such as blurred vision, double vision or loss of peripheral vision; gradual loss of sensation or movement in an arm or a leg; difficulty with balance; speech difficulties; confusion in everyday matters; personality or behavior changes; seizures, especially in someone who doesn't have a history of seizures; and hearing problems.

In some embodiments, once a differential diagnosis is made, the methods include the selection and optionally the administration of a treatment for the diagnosed disease. Thus, the methods can include selecting a treatment regimen for the subjects comprising one or more of surgical intervention, chemotherapy, and radiotherapy. For all brain cancers, the choice of therapy (e.g., surgery, radiation and/or chemotherapy) can be chosen depending on site, size, neurological function, and systemic disease status. For example, if the subject has GBM, then a treatment regime including radiation, temozolamide, and avastin may be selected and optionally administered. If the subject has metastatic brain cancer, then the treatment may depend on the source of the metastasis, i.e., on the primary cancer. For metastatic breast cancer, then the treatment could include chemotherapies approved for breast cancer (e.g., herceptin, lapatinib, doxil, or taxanes); for lung metastases, then lung cancer therapies can be selected (e.g., tarceva, alimta, or carboplatin). One of skill in the art would be able to select an appropriate treatment based on knowledge in the art. See, e.g., the National Comprehensive Cancer Network (NCCN) Guidelines, available on the internet at nccn.org.

For a subject who has been determined to have a non-neoplastic lesion using a method described herein, the methods can include monitoring the subject on a continuing basis to detect any change in the lesion, e.g., a shift to malignancy, which would be indicated by an increase in levels of miR-10b, miR-21, or miR-200.

Methods of Monitoring CNS Malignancies

The methods described herein can also be used to monitor a subject, e.g., a subject who is undergoing treatment or being followed for progression. The methods include determining levels of miR-10b, miR-21, and/or miR-200, wherein the presence of levels of miR-10b, miR-21, or miR-200 above a reference level indicate the presence of recurrence of the malignancy, and levels below the reference level indicate that the subject is in remission.

In some embodiments, e.g., for a subject who is undergoing treatment, levels of miR-10b, miR-21, and/or miR-200 can be monitored over time (e.g., by comparing levels determined from first and second, e.g., subsequent, samples taken over time; the first sample can be, but need not be, a baseline or initial sample); a decrease in levels of miR-10b, miR-21, and/or miR-200 in a subject undergoing treatment indicates that the treatment is effective. An increase in levels indicates progression. No significant change in levels indicates that no significant change has occurred, i.e., no significant change in a subject being treated that the treatment is at best slowing growth of the tumor, or is ineffective, and no significant change in a subject who is not being treated indicates that the tumor is not progressing. The presence of elevated levels in a subject who was previously in remission indicates the presence of a recurrence of the tumor, and can indicate a need for treatment.

In addition, the methods can be used to detect real progression versus pseudoprogression (a phenomenon in which a subject is observed to have experienced disease growth immediately after therapy, e.g., after radiotherapy, but are later shown to have improved or stable disease by brain imaging, see, e.g., Hoffman et al., J Neurosurg 50:624-628, 1979; Brandes et al., Clin Oncol 26:2192-2197, 2008; de Witt et al., Neurology 63:535-537, 2004; Taal et al., Cancer 113:405-410, 2008), e.g., in subjects with GBM. In the case of an apparent progression (e.g., as measured by imaging), the presence of stable or decreasing levels of miR-10b (or miR-200) as compared to earlier levels (e.g., pre-treatment levels) indicates that the apparent progression is a pseudoprogression.

The levels can be determined, e.g., before, during, or after treatment, e.g., treatment with surgery (e.g., resection or debulking), chemotherapy, or radiotherapy.

Methods of Detection

Any methods known in the art can be used to detect and/or quantify levels of a miRNA as described herein. For example, the level of a miRNA can be evaluated using methods known in the art, e.g., RT-PCR (e.g., the TAQMAN miRNA assay or similar), quantitative real time polymerase chain reaction (qRT-PCR), Northern blotting, RNA in situ hybridization (RNA-ISH), RNA expression assays, e.g., microarray analysis, deep sequencing, cloning or molecular barcoding (e.g., NANOSTRING, as described in U.S. Pat. No. 7,473,767). Analytical techniques to determine miRNA levels are known. See, e.g., Sambrook et al., *Molecular Cloning: A Laboratory Manual*, 3rd Ed., Cold Spring Harbor Press, Cold Spring Harbor, N.Y. (2001).

In some embodiments, the methods include contacting an agent that selectively binds to a biomarker, e.g., to a miRNA (such as an oligonucleotide probe that binds specifically to the miRNA) with a sample, to evaluate the level of the miRNA in the sample. In some embodiments, the agent bears a detectable label. The term "labeled," with regard to an agent encompasses direct labeling of the agent by coupling (i.e., physically linking) a detectable substance to the agent, as well as indirect labeling of the agent by reactivity with a detectable substance. Examples of detectable substances are known in the art and include chemiluminescent, fluorescent, radioactive, or colorimetric labels. For example, detectable substances can include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In some embodiments, high throughput methods, e.g., arrays (e.g., TAQMAN Array MicroRNA Cards) or gene chips as are known in the art (see, e.g., Ch. 12, "Genomics," in Griffiths et al., Eds. *Modern genetic Analysis*, 1999, W. H. Freeman and Company; Ekins and Chu, Trends in Biotechnology, 1999; 17:217-218; MacBeath and Schreiber, Science 2000, 289(5485):1760-1763; Hardiman, *Microarrays Methods and Applications: Nuts & Bolts*, DNA Press, 2003), can be used to detect the presence and/or level of a miRNA.

In some embodiments, the methods include using a modified RNA in situ hybridization technique using a branched-chain DNA assay to directly detect and evaluate the level of a miRNA in the sample (see, e.g., Luo et al., U.S. Pat. No. 7,803,541B2, 2010; Canales et al., Nature Biotechnology 24(9):1115-1122 (2006); Nguyen et al., Single Molecule in situ Detection and Direct Quantification of miRNA in Cells and FFPE Tissues, poster available at panomics.com/index.php?id=product_87). A kit for performing this assay is commercially-available from Affymetrix (ViewRNA).

Human miRNA Sequences

The following table sets forth sequences for mature human miRNAs useful in the present methods.

| Micro RNA | SEQ ID NO: | Mature Sequence |
|---|---|---|
| miR-10b | 1 | UACCCUGUAGAACCGAAUUUGUG |
| miR-21 | 2 | UAGCUUAUCAGACUGAUGUUGA |
| miR-24-1 | 3 | UGCCUACUGAGCUGAUAUCAGU |
| miR-24-2 | 4 | UGCCUACUGAGCUGAAACACAG |
| miR-200a | 5 | CAUCUUACCGGACAGUGCUGGA |
| miR-200b | 6 | CAUCUUACUGGGCAGCAUUGGA |
| miR-200c | 7 | CGUCUUACCCAGCAGUGUUUGG |
| miR-141 | 8 | CAUCUUCCAGUACAGUGUUGGA |
| miR-429 | 9 | UAAUACUGUCUGGUAAAACCGU |
| miR-125 | 10 | UCCCUGAGACCCUAACUUGUGA |

Algorithms and Computer-Implemented Methods

In some embodiments, the methods include using one or more algorithms to assign a diagnosis, based on levels of miRNAs as described herein. For example, the methods can include the use of a linear algorithm, in which one or more of the levels are weighted. In another example, the methods can include the use of a radial basis function (RBF). Appropriate linear and RBF algorithms useful in the present methods can be generated using methods known in the art, e.g., a support vector machine (SVM). The SVM was originally developed by Boser, Guyon and Vapnik ("A training algorithm for optimal margin classifiers", Fifth Annual Workshop on Computational Learning Theory, Pittsburgh, ACM (1992) pp. 142-152). See, e.g., Vapnik, "Statistical Learning Theory." John Wiley & Sons, Inc. 1998; Cristianini and Shawe-Taylor, "An Introduction to Support Vector Machines and other kernel-based learning methods." Cambridge University Press, 2000. ISBN 0-521-78019-5; and Schölkopf and Smola, "Learning with Kernels." MIT Press, Cambridge, Mass., 2002, as well as U.S. Pat. Nos. 7,475,048 and 6,882,990, all of which are incorporated herein by reference in their entirety for their teachings relating to computer systems and SVM-based methods. For example, the present methods can be performed using a computer system as described in FIG. 4 of U.S. Pat. No. 7,475,048.

EXAMPLES

The invention is further described in the following examples, which do not limit the scope of the invention described in the claims.

Materials and Methods

The following materials and methods were used in Examples 1-5, below.

Collection of Samples.

CSF and brain tumor samples were obtained from the Department of Neurosciences, UC San Diego, Moores Cancer Center, La Jolla, Calif., Department for Neurosurgery at Brigham and Women's Hospital, Boston, Mass., and from the Department for Neurosurgery at Göttingen University Medical Center, Göttingen, Germany over the period of 2-5 years. At least one ml of each CSF sample was cleared of cells and debris immediately after collection by brief centrifugation at 3000 rpm 5 min at 4° C. and stored in aliquots at −80° C. All tumor specimens were fresh-frozen on dry ice and stored at −80° C. until tested.

RNA Isolation and miRNA Profiling.

CSF samples were lyophilized and total RNA was extracted using mirVana miRNA isolation kit (Ambion) according to the manufacturer's protocol. The amount of RNA extracted from the CSF samples was within 50-2500 ng/ml range, consistent with the previous findings[3]. Total RNA from frozen tumor tissues was isolated using Trizol reagent (Invitrogen). The levels of individual miRNAs in CSF and tumors were determined by TaqMan miRNA assays from Applied Biosystems. Four ng of total RNA was used in 6 μl of reverse transcription reaction with specific miRNA RT probes, prior to TaqMan real-time PCR reactions that were performed in duplicates. MiR-125b, which is abundantly and uniformly expressed in brain, was detected in all CSF samples and used as an internal control for normalization (FIG. 5). However, since miR-125b levels themselves are not uniform across the CSF samples, both normalized and non-normalized data were considered in this study. No miRNA marker that was less variable across the CSF samples was identifiable, and generally higher miRNA CSF levels were observed in neoplastic cases relative to non-neoplastic controls. This trend may reflect a release of miRNA-containing microvesicles by cancer cells[3] and/or destruction of the brain tissue in neoplastic conditions. miRNAs levels were calculated relative to corresponding miR-125b levels by the formula $2^{\wedge}\Delta Ct$, where $\Delta Ct = Ct_{miR-125b} - Ct_{miR-X}$. All data are mean of technical duplicates, and the standard errors of mean were calculated between duplicates. Normalization to another housekeeping miRNA, miR-24, did not change the results (data not shown).

Samples Classification and Data Analysis.

A total of 118 patients of two neurooncological clinics, and corresponding CSF samples were analyzed in this study. 108 patients were classified into six groups based on clinical and pathological diagnoses (including CSF cytology and tumor histology when applicable), and magnetic resonance imaging (MRI) findings (Table 1A, the detailed patients' characteristics are listed in Table 1B). The first control group referred as "Non-neoplastic" includes patients with various neurological conditions other than brain neoplasia. The patients in this group had no cancer at the time of CSF collection, and no previous history of CNS malignancies. The second group "GBM" includes patients diagnosed with active GBM. GBM was referred to as clinically "active" when primary tumor mass was apparent by MRI imaging at the time of CSF samples collection and was further classified as GBM by tumor tissue histology. The two groups called "Breast to Brain" and "Lung to Brain" comprise of samples from the patients with parenchymal brain metastasis from breast carcinoma and lung cancer (including SCLC and NSCLC), respectively. The presence of metastases in these patients was confirmed by MRI imaging at the time of CSF collection. Two additional groups represent patients with documented leptomeningial metastasis of these cancers (CSF or MRI positive disease). Additional seven patients not included in the groups described above were analyzed separately. These patients represent cases of remission of primary and metastatic brain tumors, as indicated by no detectable brain tumor at the time of CSF collection based on imaging features, clinical stability and CSF cytology. The remaining three patients were analyzed in the longitudinal study.

TABLE 1A

Groups of patients included in this study

| Group | N | Clinical/Pathology based diagnosis |
|---|---|---|
| Control | 15 | Non-neoplastic neurological conditions: headache (4)*, trigeminal neuralgia, memory problem, gait difficulty, dementia, Parkinson disease, myelitis (2), normal pressure hydrocephalus, encephalitis, neuropathy, benign cerebellar lesion, Hodgkin disease with no CNS cancer. |
| GBM | 19 | Glioblastoma multiforme (glioma grade IV) |
| Breast to Brain | 16 | Breast cancer metastasis to brain |
| Breast LM | 26 | Breast cancer leptomeningial metastasis |
| Lung to Brain | 28 | Lung cancer metastasis to brain |
| Lung LM | 4 | Lung cancer leptomeningial metastasis |

N = number of patients per group.
*The number of patients with a particular diagnosis, if more than one, is indicated in parenthesis.

TABLE 1B

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| | Control (Non-neoplastic neurological conditions) | | | | | | |
| 1 | Non-specific pain syndrome | No tumor | Negative | 50 | F | 2005 | No surgery/LP |
| 2 | Headache | No tumor | Negative | 33 | F | 2006 | No surgery/LP |
| 3 | Memory problems, gait difficulty | No tumor | Negative | 77 | F | 2006 | No surgery/LP |
| 4 | Trigeminal neuralgia | No tumor | Negative | 67 | F | 2005 | No surgery/LP |
| 5 | Normal pressure hydrocephalus | No tumor | Negative | 80 | M | 2006 | No surgery/LP |
| 6 | Benign cerebellar lesion | No tumor | Negative | 60 | M | 2006 | Year after surgery/LP |
| 7 | Hodgkin's disease, no CNS cancer | No tumor | Negative | 33 | F | 2007 | No surgery/LP |
| 8 | Neuropathy | No tumor | Negative | 28 | F | 2007 | No surgery/LP |
| 9 | Encephalitis in patient with leukemia | No tumor | Negative | 63 | M | 2007 | No surgery/LP |

TABLE 1B-continued

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| 10 | Dementia progressive | No tumor | Negative | 44 | F | 2007 | No surgery/LP |
| 11 | Headache | No tumor | Negative | 25 | M | 2005 | No surgery/LP |
| 12 | Headache | No tumor | Negative | 40 | F | 2007 | No surgery/LP |
| 13 | Parkinson Disease | No tumor | Negative | 71 | M | 2008 | No surgery/LP |
| 14 | Transverse myelitis | No tumor | Negative | 43 | F | 2008 | No surgery/LP |
| 15 | Transverse myelitis | No tumor | Negative | 31 | F | 2008 | No surgery/LP |
| | GBM: Glioblastoma multiforme |
| 1 | GBM | IV | Negative | 55 | F | 2007 | After surgery/LP/before chemoradiation |
| 2 | GBM | IV | Positive | 27 | F | 2007 | After surgery/Ommaya/after chemoradiation |
| 3 | GBM | IV | Positive | 25 | F | 2008 | After surgery/LP/after chemoradiation |
| 4 | GBM | IV | Negative | 28 | M | 2007 | After surgery/LP/after chemoradiation |
| 5 | GBM | IV | Positive | 59 | M | 2007 | After surgery/LP/after chemoradiation |
| 6 | GBM | IV | Negative | 32 | M | 2007 | After surgery/LP/after chemoradiation |
| 7 | GBM | IV | Negative | 61 | F | 2008 | After surgery/LP/after chemoradiation |
| 8 | GBM | IV | Negative | 63 | M | 2009 | After surgery/LP/after chemoradiation |
| 9 | GBM | IV | NA | NA | NA | 2008 | During surgery/Ommaya/before chemoradiation |
| 10 | GBM | IV | NA | NA | NA | 2008 | During surgery/Ommaya before chemoradiation |
| 11 | GBM | IV | NA | NA | NA | 2008 | During surgery/Ommaya before chemoradiation |
| 12 | GBM | IV | NA | NA | NA | 2008 | During surgery/Ommaya before chemoradiation |
| 13 | GBM | IV | NA | NA | NA | 2008 | During surgery/Ommaya before chemoradiation |
| 14 | GBM | IV | NA | NA | NA | 2008 | During surgery/Ommaya before chemoradiation |
| 15 | GBM | IV | NA | NA | NA | 2008 | During surgery/Ommaya before chemoradiation |
| 16 | GBM | IV | NA | NA | NA | 2008 | During surgery/Ommaya before chemoradiation |
| 17 | GBM | IV | NA | NA | NA | 2008 | During surgery/Ommaya before chemoradiation |
| 18 | GBM | IV | Negative | 61 | F | 2005 | After surgery/LP/after chemoradiation |
| 19 | GBM | IV | NA | 43 | F | 2010 | After surgery/LP/before chemoradiation |
| | Breast to Brain: breast cancer brain metastasis |
| 1 | Breast carcinoma brain metastasis | IV | Positive | 55 | F | 2008 | No surgery/LP/after radiation and during chemotherapy |
| 2 | Breast carcinoma brain metastasis | IV | Positive | 63 | F | 2008 | After surgery/Ommaya/after radiation and during chemotherapy |
| 3 | Breast carcinoma brain metastasis | IV | Positive | 54 | F | 2008 | No surgery/LP/after radiation and during chemotherapy |

TABLE 1B-continued

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| 4 | Breast carcinoma brain metastasis | IV | Positive | 60 | F | 2008 | After surgery/Ommaya/after radiation and during chemotherapy |
| 5 | Breast carcinoma brain metastasis | IV | Positive | 55 | F | 2008 | After surgery/Ommaya/after radiation and during chemotherapy |
| 6 | Breast carcinoma brain metastasis | IV | Positive | 62 | F | 2008 | After surgery/Ommaya/after radiation and during chemotherapy |
| 7 | Breast carcinoma brain metastasis | IV | Positive | 54 | F | 2008 | After surgery/Ommaya/after radiation and during chemotherapy |
| 8 | Breast carcinoma brain metastasis | IV | Positive | 60 | F | 2008 | After surgery/LP/after radiation and during chemotherapy |
| 9 | Breast carcinoma brain metastasis | IV | Positive | 54 | F | 2008 | After surgery/Ommaya/after radiation and during chemotherapy |
| 10 | Breast carcinoma brain metastasis | IV | Positive | 52 | F | 2008 | No surgery/after radiation and during chemotherapy |
| 11 | Breast carcinoma brain metastasis | IV | Positive | 65 | F | 2008 | After surgery/Ommaya/after radiation and during chemotherapy |
| 12 | Breast carcinoma brain metastasis | IV | Positive | 48 | F | 2008 | After surgery/Ommaya/after radiation and during chemotherapy |
| 13 | Breast carcinoma brain metastasis | IV | Positive | 46 | F | 2008 | After surgery/LP/after radiation and during chemotherapy |
| 14 | Breast carcinoma brain metastasis | IV | Atypical | 50 | F | 2008 | After surgery/LP/after radiation and during chemotherapy |
| 15 | Breast carcinoma brain metastasis | IV | Positive | 55 | F | 2008 | After surgery/LP/after radiation and during chemotherapy |
| 16 | Breast carcinoma brain metastasis | IV | Positive | 57 | F | 2008 | After surgery/LP/after radiation and during chemotherapy |
| Breast LM: breast cancer leptomeningial metastasis | | | | | | | |
| 1 | Breast carcinoma leptomeningial metastasis | IV | Negative | 42 | F | 2006 | No surgery/LP/after radiation |
| 2 | Breast carcinoma leptomeningial metastasis | IV | Positive | 60 | F | 2007 | After surgery/Ommaya/after radiation and during chemotherapy |
| 3 | Breast carcinoma leptomeningial metastasis | IV | Positive | 59 | F | 2007 | After surgery/Ommaya/after radiation and during chemotherapy |
| 4 | Breast carcinoma leptomeningial metastasis | IV | Positive | 61 | F | 2007 | After surgery/Ommaya/after radiation and during chemotherapy |
| 5 | Breast carcinoma leptomeningial metastasis | IV | Positive | 64 | F | 2007 | After surgery/Ommaya/after radiation and during chemotherapy |
| 6 | Breast carcinoma leptomeningial metastasis | IV | Positive | 53 | F | 2007 | After surgery/Ommaya/after radiation and during chemotherapy |
| 7 | Breast carcinoma leptomeningial metastasis | IV | Positive | 66 | F | 2007 | No surgery/LP/after radiation |

TABLE 1B-continued

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| 8 | Breast carcinoma leptomeningial metastasis | IV | Positive | 54 | F | 2007 | After surgery/Ommaya/ after radiation and during chemotherapy |
| 9 | Breast carcinoma leptomeningial metastasis | IV | Positive | 60 | F | 2007 | After surgery/Ommaya/ after radiation and during chemotherapy |
| 10 | Breast carcinoma leptomeningial metastasis | IV | Positive | 63 | F | 2007 | After surgery/Ommaya/ after radiation and during chemotherapy |
| 11 | Breast carcinoma leptomeningial metastasis | IV | Positive | 66 | F | 2007 | After surgery/Ommaya/ after radiation and during chemotherapy |
| 12 | Breast carcinoma leptomeningial metastasis | IV | Positive | 60 | F | 2007 | After surgery/Ommaya/ after radiation and during chemotherapy |
| 13 | Breast carcinoma leptomeningial metastasis | IV | Positive | 55 | F | 2007 | After surgery/Ommaya/ after radiation and during chemotherapy |
| 14 | Breast carcinoma leptomeningial metastasis | IV | Positive | 56 | F | 2007 | After surgery/Ommaya/ after radiation and during chemotherapy |
| 15 | Breast carcinoma leptomeningial metastasis | IV | Positive | 44 | F | 2007 | After surgery/Ommaya/after radiation and during chemotherapy |
| 16 | Breast carcinoma leptomeningial metastasis | IV | Positive | 58 | F | 2007 | After surgery/Ommaya/ after radiation and during chemotherapy |
| 17 | Breast carcinoma leptomeningial metastasis | IV | Positive | 54 | F | 2007 | No surgery/LP/after radiation and during chemotherapy |
| 18 | Breast carcinoma leptomeningial metastasis | IV | Negative | 45 | F | 2007 | No surgery/LP/after radiation and during chemotherapy |
| 19 | Breast carcinoma leptomeningial metastasis | IV | Negative | 60 | F | 2008 | No surgery/LP/after radiation and during chemotherapy |
| 20 | Breast carcinoma leptomeningial metastasis | IV | Positive | 51 | F | 2008 | After surgery/Ommaya/ after radiation and during chemotherapy |
| 21 | Breast carcinoma leptomeningial metastasis | IV | Positive | 29 | F | 2008 | No surgery/LP/after radiation and during chemotherapy |
| 22 | Breast carcinoma leptomeningial metastasis | IV | Positive | 69 | F | 2008 | No surgery/LP/after radiation and during chemotherapy |
| 23 | Breast carcinoma leptomeningial metastasis | IV | Positive | 61 | F | 2008 | NA |
| 24 | Breast carcinoma leptomeningial metastasis | IV | Positive | 64 | F | 2008 | No surgery/LP/after radiation and during chemotherapy |
| 25 | Breast carcinoma leptomeningial metastasis | IV | Positive | 63 | F | 2008 | No surgery/LP |
| 26 | Breast carcinoma leptomeningial metastasis | IV | Positive | 59 | F | 2008 | After surgery/Ommaya/ after radiation and during chemotherapy |
| Lung to Brain: lung cancer brain metastasis | | | | | | | |
| 1 | Lung cancer brain metastasis | IV | Positive | 56 | F | 2007 | No surgery/LP/after radiation and during chemotherapy |

TABLE 1B-continued

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| 2 | Lung cancer brain metastasis | IV | Positive | 59 | F | 2007 | No surgery/LP/after radiation and during chemotherapy |
| 3 | Lung cancer brain metastasis | IV | Positive | 56 | F | 2007 | No surgery/LP/after radiation and during chemotherapy |
| 4 | Lung cancer brain metastasis | IV | Positive | 68 | F | 2007 | No surgery/LP |
| 5 | Lung cancer brain metastasis | IV | Positive | 69 | M | 2007 | No surgery/LP/after radiation |
| 6 | Lung cancer brain metastasis | IV | Positive | 71 | M | 2007 | No surgery/LP/after radiation and during chemotherapy |
| 7 | Lung cancer brain metastasis | IV | Positive | 66 | F | 2007 | No surgery/LP/after radiation and during chemotherapy |
| 8 | Lung cancer brain metastasis | IV | Positive | 63 | F | 2007 | No surgery/LP/after radiation and during chemotherapy |
| 9 | Lung cancer brain metastasis | IV | Positive | 60 | F | 2007 | No surgery/LP/after radiation and during chemotherapy |
| 10 | Lung cancer brain metastasis | IV | Positive | 59 | F | 2007 | No surgery/LP |
| 11 | Lung cancer brain metastasis | IV | Positive | 55 | M | 2008 | No surgery/LP |
| 12 | NSCLC brain metastasis | IV | Negative | 66 | F | 2008 | No surgery/LP |
| 13 | Lung cancer brain metastasis | IV | Positive | 62 | F | 2007 | No surgery/LP/after radiation and during chemotherapy |
| 14 | Lung cancer brain metastasis | IV | Positive | 64 | F | 2006 | No surgery/LP |
| 15 | Lung cancer brain metastasis | IV | Positive | 64 | F | 2006 | No surgery/LP |
| 16 | Lung cancer brain metastasis | IV | Negative | 46 | F | 2007 | No surgery/LP |
| 17 | Lung cancer brain metastasis | IV | Positive | 64 | F | 2007 | No surgery/LP |
| 18 | NSLC brain metastasis | IV | Negative | 50 | M | 2007 | No surgery/LP |
| 19 | NSCLC brain metastasis | IV | Positive | 56 | M | 2007 | No surgery/LP/after radiation and during chemotherapy |
| 20 | NSCLC brain metastasis | IV | Positive | 49 | F | 2007 | No surgery/LP/after radiation and during chemotherapy |
| 21 | Lung cancer brain metastasis | IV | Positive | 42 | M | 2007 | No surgery/LP/after radiation and during chemotherapy |
| 22 | Lung cancer brain metastasis | IV | Positive | 56 | F | 2007 | No surgery/LP/after radiation and during chemotherapy |
| 23 | Lung cancer brain metastasis | IV | Positive | 58 | F | 2008 | No surgery/LP/after radiation and during chemotherapy |
| 24 | NSCLC brain metastasis | IV | Positive | 48 | M | 2008 | No surgery/LP |
| 25 | MSCLC brain metastasis | IV | Negative | 54 | F | 2008 | No surgery/LP |
| 26 | NSCLC brain metastasis | IV | Negative | 61 | F | 2008 | No surgery/LP |
| 27 | NSCLC brain metastasis | IV | NA | 51 | F | 2010 | After surgery/Ommaya after radiation and during chemotherapy |
| 28 | NSCLC brain metastasis | IV | NA | 66 | F | 2010 | No surgery/LP after radiation and during chemotherapy |
| Lung LM: lung cancer leptomeningial metastasis | | | | | | | |
| 1 | Lung cancer leptomeningial metastasis | IV | Positive | 67 | F | 2006 | No surgery/LP |

TABLE 1B-continued

Neurological diagnosis and individual characteristics of patients included in CSF microRNA analysis

| ## | Clinical/Pathology based diagnosis | Tumor grade | CSF cytology | Age | Gender | Year of sample collection | Time/way of sample collection |
|---|---|---|---|---|---|---|---|
| 2 | SCLC leptomeningial metastasis | IV | Negative | 52 | M | 2007 | No surgery/LP |
| 3 | Lung cancer leptomeningial metastasis | IV | Negative | 56 | F | 2008 | No surgery/LP |
| 4 | NSCLC leptomeningial metastasis | IV | NA | 63 | M | 2010 | No surgery/LP/after radiation and chemotherapy |

NA = not available,
NSCLC—non-small cell lung carcinoma,
SCLC—small cell lung carcinoma/

Statistical Analysis and Support Vector Machine (SVM)-Based Data Classification.

The differences in CSF miRNAs levels between groups of samples were determined using Graph Pad Prism software by Wilcoxon Signed Rank test, and two-tailed P-values were calculated.

SVM was implemented within a machine learning software package weka (Witten, "Data Mining: Practical machine learning tools and techniques, 3rd Edition". Morgan Kaufmann, San Francisco (2011)), available on the internet at cs.waikato.ac.nz/ml/weka. In such an approach, a sample's miRNA levels were treated as independent variables and the type of cancer, if any, as a variable to be predicted. The SVM was trained and tested on such a dataset, using standard N-fold cross-validation process. In this process the SVM was trained on all samples, except for one, and tested on that holdout sample. The procedure was repeated as many times as there were samples in the dataset, hence each sample once and only once forms the holdout set. The following choices of non-default parameters working best: Classifier: SMO, kernel RBF, Complexity parameter=one for all tasks, except breast vs. lung metastasis, in which case it was 100. Ct data were used for the classification as is, with no standardization or normalization, except "1000" was used on the place of Ct values in the cases of undetectable miRNA.

The Cancer Genome Atlas (TCGA) miRNA expression microarray data for GBM patients were downloaded from tcga-data.nci.nih.gov/tcga/homepage.htm; see Hudson et al., Nature 464:993-998 (2010). The fold difference in specific signals between GBM (n=261) and normal brain (n=10) tissue were calculated for each miRNA as described[3].

Figure 1B:
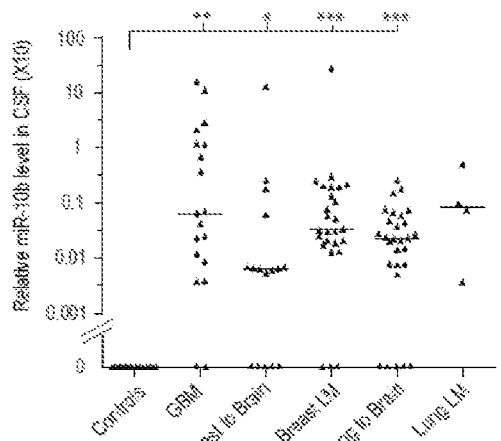

Example 1 miR-10b is Present and miR-21 is Elevated in CSF of Glioblastoma and Brain Metastasis Patients To identify miRNA biomarkers for GBM, a candidate approach was used based on previous miRNA profiling data[3,14,15]. An additional analysis of miRNA expression in 261 GBM patients utilized The Cancer Genome Atlas (TCGA) dataset (Hudson et al., Nature 464:993-998 (2010)) and revealed a panel of miRNAs deregulated in GBM relative to normal brain tissues (FIG. 1A). Among them, miR-10b and miR-21 were the most strongly up-regulated (FIG. 1A). miR-10b is a unique molecule, as it is the only known miRNA undetectable in normal brain while highly expressed in GBM[16,17]. It was therefore chosen as the top priority candidate. Expression of miR-10b is also associated with metastatic phenotypes of several solid cancers, including breast and lung cancers[18,19].

miR-10b levels were examined in the CSF samples of the study cohort patients, and miR-10b-specific qRT-PCR product was detected in CSF of 17 out of 19 GBM patients (89% cases, FIG. 1B). This is consistent with previous finding of miR-10b expression in ~90% of GBM tumors[15]. miR-10b was also detected in CSF of 81% of patients with brain and leptomeningeal metastasis of both breast and lung cancer (FIG. 1B). None of the patients with various non-neoplastic neurological conditions showed detectable levels of miR-10b at 40 cycles of the qRT-PCR reaction. Raw qRT-PCR Ct values representing specific CSF levels of miR-10b and other miRNAs are shown in Table 2B. Therefore, miR-10b in CSF is a highly indicative marker of high-grade primary and metastatic brain cancers.

Figure 1C:
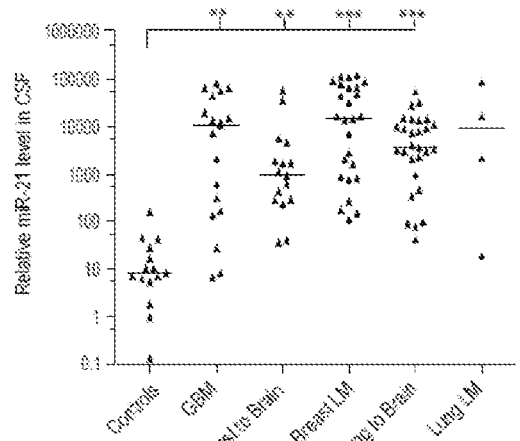

Next CSF levels were assessed for another candidate miRNA, miR-21, which is the most common miRNA elevated in GBM and other cancers[20] and also most strongly up-regulated in GBM as compared to normal brain (FIG. 1A). miR-21 levels are significantly increased in CSF of most GBM and metastatic patients relatively to its levels in the control CSF samples (FIG. 1C), suggesting that it may represent an additional CSF biomarker for both GBM and metastatic brain cancer.

Figure 6A:
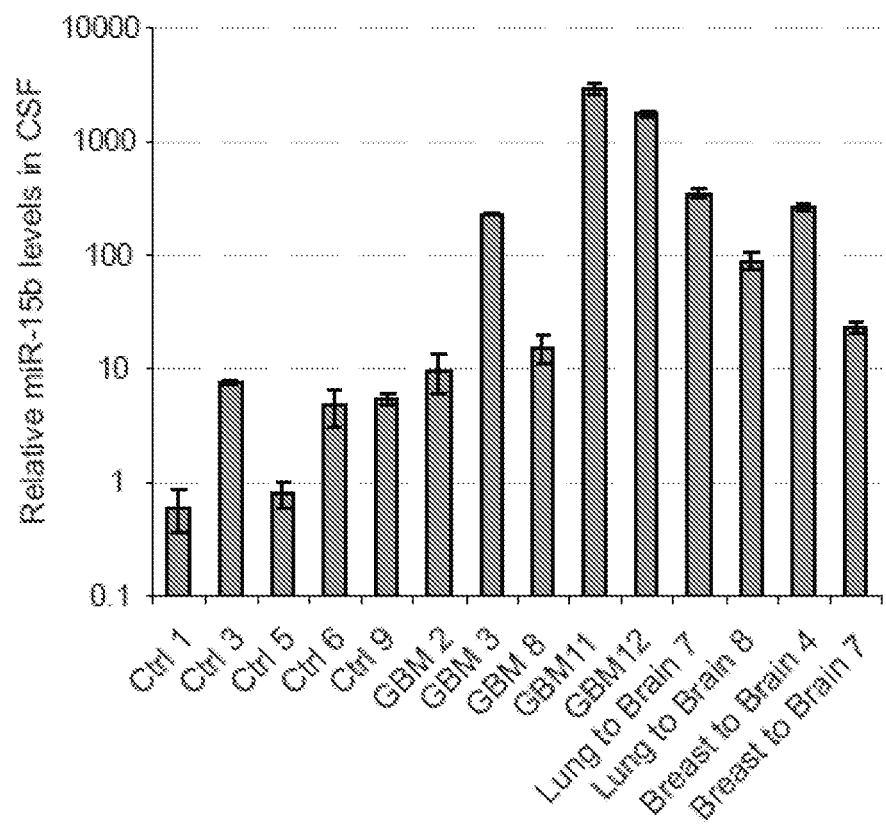
FIGS. 6A-F are graphs showing miRNA levels in CSF of randomly selected patients with GBM, metastatic brain cancers and non-neoplastic controls are demonstrated for: (6A) miR-15b, (6B) miR-15b normalized to miR-125b, (6C) miR-17-5p, (6D) miR-17-5p normalized to miR-125b, (6E) miR-93, (6F) miR-93 normalized to miR-125b. miRNA levels in CSF samples were determined by qRT-PCR reaction. Relative miRNA levels were quantified by the ΔCt method and normalized to miR-125b as described in Materials and methods. Error bars represent standard error of mean between technical duplicates.
Figure 6B:
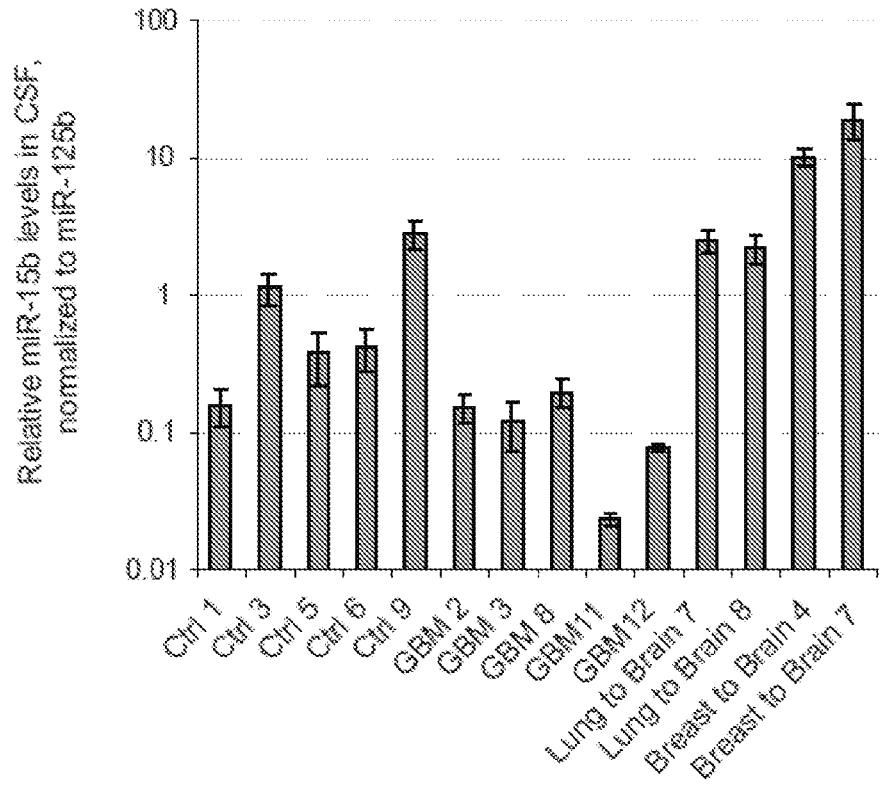
Figure 6C:
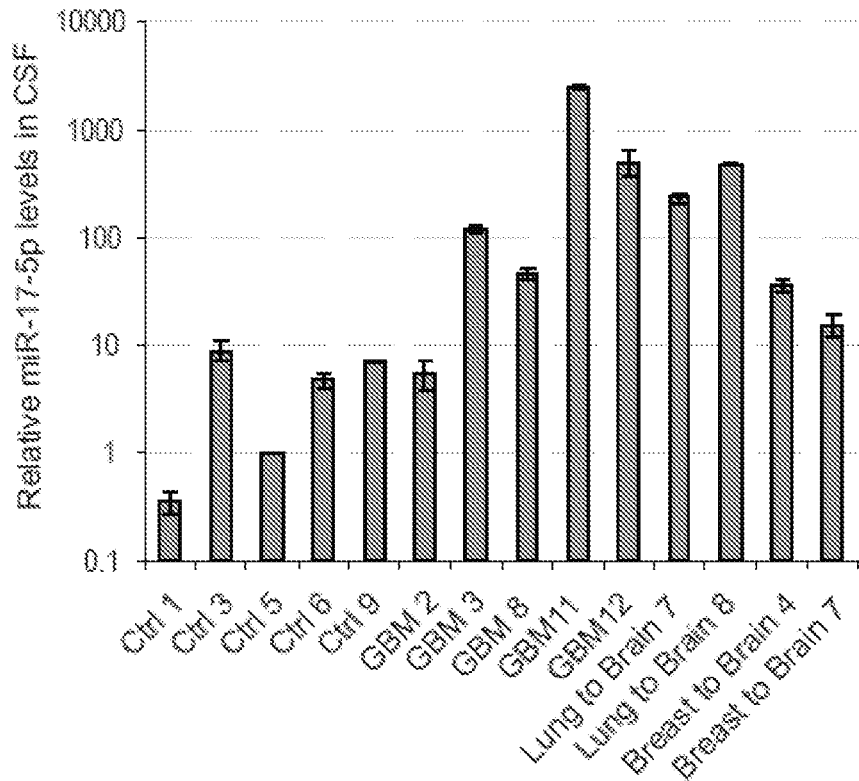
Figure 6D:
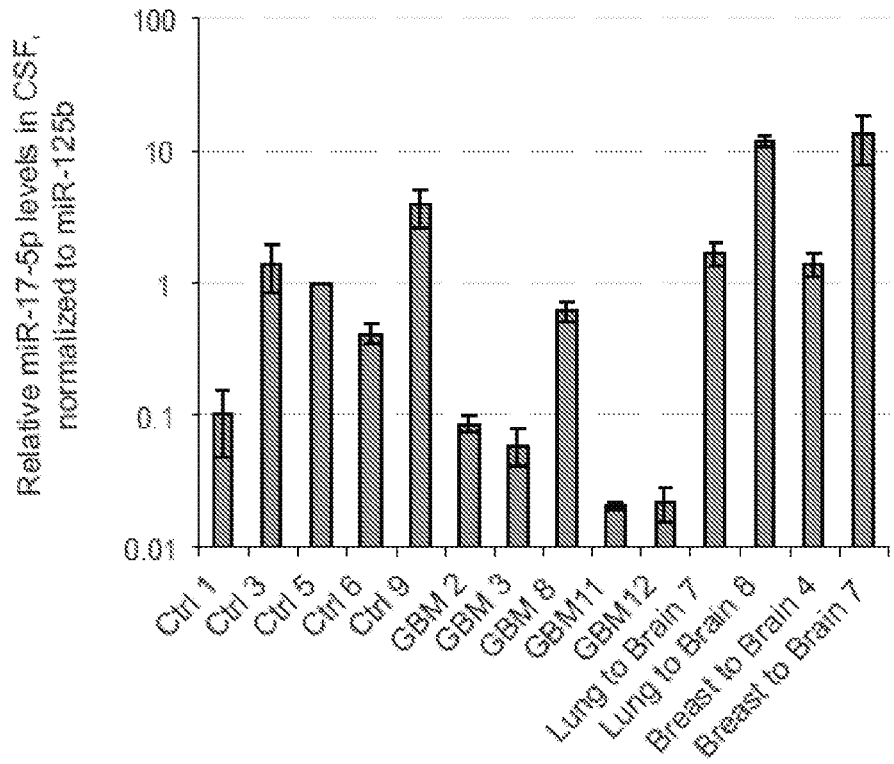
Figure 6E:
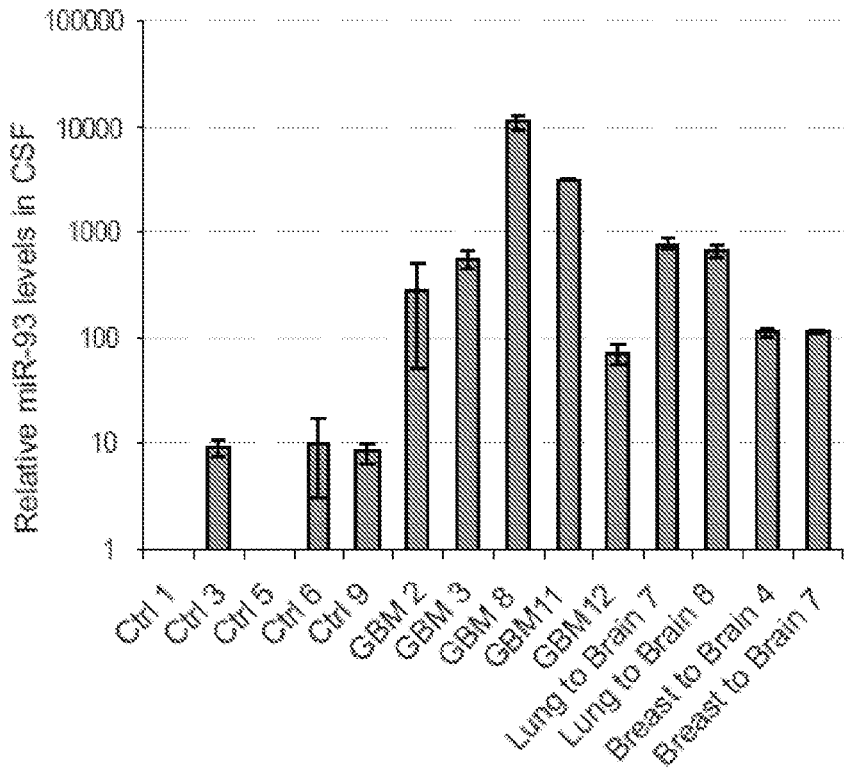
Figure 6F:
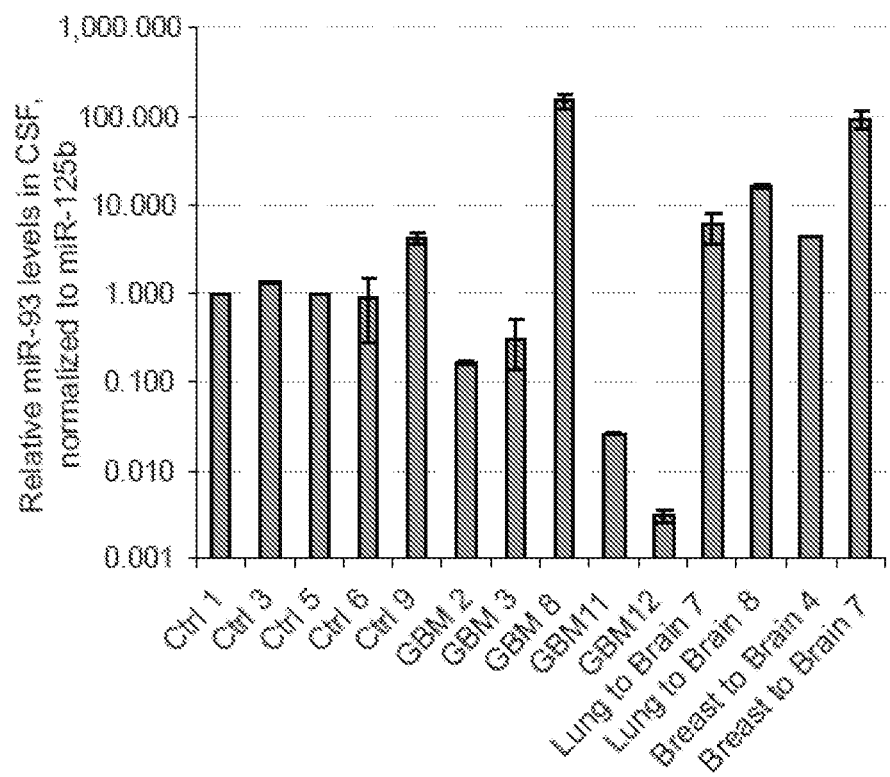

The levels of three additional candidate miRNAs upregulated in GBM relative to normal brain, miR-15b, miR-17-5p and miR-93 (FIG. 1A), have been determined in a randomly selected set of several CSF samples. The levels of all three miRNAs were higher in CSF of GBM and metastatic brain cancer patients relatively to the non-neoplastic controls (FIGS. 6A, C, E); however, these differences have not reached the significance and were abolished by data normalization to miR-125b (FIGS. 6B, D, F).

TABLE 2A

Accuracies of classification of brain tumors by SVM analysis.

| | Instances classified in the test sets | |
|---|---|---|
| Comparison | Correctly | Incorrectly |
| GBM versus non-neoplastic controls | 31 (91.2%) | 3 (8.8%) |
| Metastasis versus non-neoplastic controls | 88 (98.9%) | 1 (1.1%) |
| GBM and metastasis versus non-neoplastic controls | 105 (97.2%) | 3 (2.8%) |
| GBM versus metastasis | 89 (95.7%) | 4 (4.3%) |
| GBM versus non-GBM (all others) | 102 (94.5%) | 6 (5.5%) |
| Metastasis versus non-metastasis (all others) | 100 (92.6%) | 8 (7.4%) |
| Breast versus lung metastasis | 51 (68.9%) | 23 (31.1%) |

TABLE 2B

| | | miRNA | | | | | | |
|---|---|---|---|---|---|---|---|---|
| Type | # | 125b | 10b | 21 | 141 | 200a | 200b | 200c |
| Non-neoplastic | 1 | 34.2697 | UD | 33.3324 | UD | UD | UD | UD |
| Non-neoplastic | 1 | 33.9405 | UD | 33.0829 | UD | UD | UD | UD |
| Non-neoplastic | 2 | 33.0152 | UD | 33.5002 | UD | UD | UD | UD |
| Non-neoplastic | 2 | 32.799 | UD | 32.9746 | UD | UD | UD | UD |
| Non-neoplastic | 3 | 32.9036 | UD | 33.707 | UD | UD | UD | UD |
| Non-neoplastic | 3 | 33.5036 | UD | 33.5222 | UD | UD | UD | UD |
| Non-neoplastic | 4 | 32.1067 | UD | 32.5033 | UD | UD | UD | UD |
| Non-neoplastic | 4 | 32.2493 | UD | 32.8214 | UD | UD | UD | UD |
| Non-neoplastic | 5 | 33.8516 | UD | 33.258 | UD | UD | UD | UD |
| Non-neoplastic | 5 | 35.8576 | UD | 32.7309 | UD | UD | UD | UD |
| Non-neoplastic | 6 | 32.4644 | UD | 28.6672 | UD | UD | UD | UD |
| Non-neoplastic | 6 | 32.4621 | UD | 28.7054 | UD | UD | UD | UD |
| Non-neoplastic | 7 | 31.6864 | UD | 35.2616 | UD | 37.4531 | UD | UD |
| Non-neoplastic | 7 | 32.1712 | UD | 35.0806 | UD | 37.2431 | UD | UD |
| Non-neoplastic | 8 | 32.0006 | UD | 32.1841 | UD | UD | UD | UD |
| Non-neoplastic | 8 | 31.7911 | UD | 31.7029 | UD | UD | UD | UD |
| Non-neoplastic | 9 | 34.5177 | UD | 30.3603 | UD | UD | UD | UD |
| Non-neoplastic | 9 | 35.5515 | UD | 30.6514 | UD | UD | UD | UD |
| Non-neoplastic | 10 | 32.5169 | UD | 32.9137 | UD | UD | UD | UD |
| Non-neoplastic | 10 | 32.781 | UD | 32.3816 | UD | UD | UD | UD |
| Non-neoplastic | 11 | 30.661 | UD | 30.635 | UD | UD | UD | UD |
| Non-neoplastic | 11 | 30.706 | UD | 30.528 | UD | UD | UD | UD |
| Non-neoplastic | 12 | 30.396 | UD | 30.993 | UD | UD | UD | UD |
| Non-neoplastic | 12 | 30.159 | UD | 31.398 | UD | UD | UD | UD |
| Non-neoplastic | 13 | 29.798 | UD | 38.9142 | UD | UD | UD | UD |
| Non-neoplastic | 13 | 29.469 | UD | 38.9142 | UD | UD | UD | UD |
| Non-neoplastic | 14 | 37.111 | UD | 36.431 | UD | UD | UD | UD |
| Non-neoplastic | 14 | 36.750 | UD | 35.824 | UD | UD | UD | UD |
| Non-neoplastic | 15 | 32.311 | UD | 33.307 | UD | UD | UD | UD |
| Non-neoplastic | 15 | 31.782 | UD | 33.483 | UD | UD | UD | UD |
| GBM | 1 | 28.493 | 35.4474 | 24.8591 | UD | UD | UD | UD |
| GBM | 1 | 28.3347 | 36.1669 | 25.0358 | UD | UD | UD | UD |
| GBM | 2 | 30.27 | UD | 28.5448 | UD | UD | UD | UD |
| GBM | 2 | 29.8595 | UD | 28.7406 | UD | UD | UD | UD |
| GBM | 3 | 25.5607 | 33.3961 | 22.0836 | 36.807 | 33.5488 | 36.6658 | 36.6814 |
| GBM | 3 | 24.3582 | 33.0576 | 22.1982 | 35.7105 | 33.2086 | 37.0597 | 37.1643 |
| GBM | 4 | 24.9425 | 37.8446 | 23.4126 | UD | 35.597 | UD | 34.1835 |
| GBM | 4 | 24.8871 | 37.0681 | 22.9477 | UD | 35.0309 | UD | 34.1049 |
| GBM | 5 | 34.2504 | UD | 33.3238 | UD | UD | UD | UD |
| GBM | 5 | 34.4141 | UD | 33.2358 | UD | UD | UD | UD |
| GBM | 6 | 25.9917 | 36.2066 | 21.9135 | UD | 35.2526 | UD | UD |
| GBM | 6 | 25.7625 | 36.2066 | 21.6147 | UD | 34.1246 | UD | UD |
| GBM | 7 | 29.2959 | 33.4857 | 29.3222 | UD | 37.1513 | UD | UD |
| GBM | 7 | 29.1532 | 33.1848 | 28.6781 | UD | 36.9511 | UD | UD |
| GBM | 8 | 29.7628 | 30.8808 | 33.2773 | UD | UD | UD | UD |
| GBM | 8 | 29.6696 | 30.7112 | 32.7008 | UD | UD | UD | UD |
| GBM | 9 | 29.5463 | 36.926 | 22.4494 | 28.5888 | UD | 31.3221 | UD |
| GBM | 9 | 29.8912 | 38.0723 | 22.4455 | 29.173 | UD | 31.7444 | UD |
| GBM | 10 | 18.8301 | 28.2565 | 21.3035 | 34.1768 | 30.673 | 35.202 | 30.9622 |
| GBM | 10 | 19.1781 | 28.3153 | 20.1106 | 35.3052 | 31.3501 | 34.5208 | 32.0136 |
| GBM | 11 | 19.0653 | 25.3992 | 19.9446 | 35.7793 | 30.3237 | 34.3587 | 35.3505 |
| GBM | 11 | 19.0975 | 25.3985 | 20.5917 | 35.4663 | 29.8643 | 34.234 | 36.6375 |
| GBM | 12 | 21.4785 | 29.5007 | 22.5529 | 34.3938 | 32.3403 | 36.3228 | 33.6589 |
| GBM | 12 | 21.4785 | 30.5404 | 22.0745 | 35.6437 | 32.8565 | 35.9838 | 33.3638 |
| GBM | 13 | 20.6069 | 28.0427 | 22.8669 | 38.4408 | 29.7108 | 34.4638 | 31.5322 |
| GBM | 13 | 21.1061 | 27.6744 | 22.4195 | 36.4015 | 31.1373 | 33.8695 | 32.1085 |
| GBM | 14 | 20.5726 | 29.0133 | 19.8893 | 35.0699 | 31.0412 | 35.4186 | 32.4751 |
| GBM | 14 | 20.4409 | 29.2476 | 20.1753 | 36.0567 | 31.5226 | 35.4393 | 33.3155 |
| GBM | 15 | 28.0429 | 34.4698 | 31.1034 | UD | UD | UD | UD |
| GBM | 15 | 28.3493 | 34.9682 | 31.2799 | UD | UD | UD | UD |
| GBM | 16 | 18.9454 | 29.2594 | 20.2101 | 33.9212 | UD | 34.7543 | 30.0307 |
| GBM | 16 | 19.0949 | 29.0995 | 19.8017 | 34.5306 | UD | 34.0056 | 31.1451 |
| GBM | 17 | 19.0563 | 25.713 | 19.6841 | 35.3343 | 28.5198 | 31.2043 | 31.0678 |
| GBM | 17 | 19.3106 | 26.0705 | 19.6881 | 35.0194 | 29.3597 | 31.4789 | 31.798 |
| GBM | 18 | 31.138 | 34.459 | 26.774 | UD | UD | UD | UD |
| GBM | 18 | 31.555 | 35.215 | 26.695 | UD | UD | UD | UD |
| GBM | 19 | 28.157 | 33.496 | 27.861 | UD | UD | UD | UD |
| GBM | 19 | 27.883 | 34.539 | 27.602 | UD | UD | UD | UD |
| Breast to Brain | 1 | 27.8174 | 32.0139 | 21.1639 | 29.5078 | 26.0618 | 31.4264 | 27.1292 |
| Breast to Brain | 1 | 27.2568 | 31.706 | 20.675 | 29.3259 | 26.2505 | 30.9209 | 27.7123 |
| Breast to Brain | 2 | 32.6303 | UD | 28.0095 | 37.1365 | 31.0578 | 32.6672 | 31.5072 |
| Breast to Brain | 2 | 32.5818 | UD | 27.7492 | 37.6775 | 31.0501 | 32.4441 | 31.8525 |
| Breast to Brain | 3 | 25.7808 | 31.3092 | 20.1414 | 29.1359 | 27.1009 | 30.5338 | 28.0328 |
| Breast to Brain | 3 | 25.977 | 31.3399 | 20.1774 | 29.2168 | 26.8024 | 30.2247 | 28.4686 |
| Breast to Brain | 4 | 31.1532 | 38.8239 | 23.4787 | 32.0578 | 26.4437 | 29.4728 | 30.6951 |
| Breast to Brain | 4 | 31.3755 | UD | 23.5862 | 32.8802 | 26.9978 | 29.1922 | 31.5229 |

TABLE 2B-continued

| | | miRNA | | | | | | |
|---|---|---|---|---|---|---|---|---|
| Type | # | 125b | 10b | 21 | 141 | 200a | 200b | 200c |
| Breast to Brain | 5 | 29.6268 | 36.8038 | 25.6345 | 29.8542 | 24.483 | 27.1907 | 28.9925 |
| Breast to Brain | 5 | 30.2187 | 36.262 | 25.0105 | 32.3864 | 24.483 | 27.2909 | 29.4038 |
| Breast to Brain | 6 | 30.3481 | UD | 25.5752 | 30.7873 | 24.67 | 28.5216 | 26.9064 |
| Breast to Brain | 6 | 30.709 | UD | 27.1514 | 31.7873 | 24.7185 | 28.2027 | 26.8947 |
| Breast to Brain | 7 | 35.4251 | 36.5204 | 28.0536 | 32.7134 | 27.8074 | 30.2571 | 32.2786 |
| Breast to Brain | 7 | 35.9251 | 36.5204 | 28.2612 | 32.3935 | 28.0258 | 29.9113 | 33.1268 |
| Breast to Brain | 8 | 30.5423 | 36.5667 | 27.8147 | 32.3054 | 29.5245 | 32.3943 | 29.0791 |
| Breast to Brain | 8 | 30.1858 | 36.8752 | 27.8631 | 32.1674 | 29.9147 | 32.5332 | 28.0088 |
| Breast to Brain | 9 | 32.1644 | UD | 25.9139 | 31.7038 | 28.1264 | 30.3435 | 30.0191 |
| Breast to Brain | 9 | 33.1737 | UD | 25.8558 | 32.1792 | 28.1041 | 30.1035 | 30.2432 |
| Breast to Brain | 10 | 28.3774 | 37.1231 | 25.108 | 28.4444 | 27.2268 | 31.0834 | 26.2144 |
| Breast to Brain | 10 | 28.8228 | 36.1869 | 25.0972 | 28.835 | 26.5499 | 31.1109 | 25.9687 |
| Breast to Brain | 11 | 33.2952 | UD | 30.864 | UD | 33.4073 | 38.1796 | 33.7632 |
| Breast to Brain | 11 | 32.6806 | UD | 30.8002 | UD | 35.7065 | 37.0988 | 33.3951 |
| Breast to Brain | 12 | 30.044 | 32.846 | 25.180 | 30.020 | 30.641 | 32.699 | 29.391 |
| Breast to Brain | 12 | 29.709 | 34.234 | 25.414 | 30.461 | 30.452 | 32.992 | 30.033 |
| Breast to Brain | 13 | 30.368 | 36.826 | 27.307 | 33.816 | 33.117 | 35.072 | 31.908 |
| Breast to Brain | 13 | 30.417 | 36.920 | 27.261 | 33.340 | 32.604 | 35.081 | 32.021 |
| Breast to Brain | 14 | 21.508 | 25.708 | 23.920 | 35.289 | 35.603 | 35.800 | 34.705 |
| Breast to Brain | 14 | 21.414 | 25.617 | 23.742 | 36.763 | 35.476 | 38.213 | 34.781 |
| Breast to Brain | 15 | 29.378 | 36.876 | 26.886 | 30.667 | 30.539 | 32.789 | 29.405 |
| Breast to Brain | 15 | 29.457 | 36.376 | 26.601 | 30.678 | 30.333 | 32.183 | 29.738 |
| Breast to Brain | 16 | 30.966 | 36.324 | 30.592 | 34.492 | 34.035 | 36.778 | 32.881 |
| Breast to Brain | 16 | 30.699 | 37.014 | 30.740 | 34.933 | 33.617 | 36.980 | 32.690 |
| Breast LM | 1 | 30.631 | 35.604 | 28.651 | 35.954 | 35.557 | UD | 35.152 |
| Breast LM | 1 | 30.519 | 35.568 | 28.452 | 37.282 | 35.763 | 38.580 | UD |
| Breast LM | 2 | 26.997 | 34.318 | 20.781 | 29.000 | 26.659 | 28.954 | 27.883 |
| Breast LM | 2 | 26.886 | 34.178 | 20.395 | 29.111 | 26.412 | 28.871 | 28.265 |
| Breast LM | 3 | 24.423 | 31.054 | 19.165 | 27.767 | 25.225 | 27.433 | 26.237 |
| Breast LM | 3 | 24.284 | 31.130 | 18.992 | 27.967 | 25.008 | 27.407 | 26.622 |
| Breast LM | 4 | 28.283 | 35.548 | 22.324 | 30.800 | 26.526 | 30.470 | 29.647 |
| Breast LM | 4 | 28.123 | 34.502 | 22.095 | 30.900 | 26.425 | 30.638 | 29.759 |
| Breast LM | 5 | 24.748 | 31.465 | 19.238 | 29.508 | 26.466 | 28.156 | 27.618 |
| Breast LM | 5 | 24.735 | 31.253 | 19.162 | 29.591 | 26.347 | 28.039 | 27.623 |
| Breast LM | 6 | 25.164 | 31.746 | 19.547 | 29.870 | 27.440 | 28.653 | 28.036 |
| Breast LM | 6 | 25.097 | 31.742 | 19.467 | 30.269 | 27.271 | 28.579 | 28.192 |
| Breast LM | 7 | 31.297 | 34.899 | 28.895 | 38.345 | 36.188 | UD | 28.182 |
| Breast LM | 7 | 31.275 | 34.054 | 28.710 | 38.815 | 36.763 | UD | 28.202 |
| Breast LM | 8 | 25.550 | 31.414 | 20.539 | 30.363 | 28.001 | 30.203 | 29.081 |
| Breast LM | 8 | 25.382 | 31.941 | 20.389 | 31.110 | 28.097 | 29.728 | 29.224 |
| Breast LM | 9 | 25.436 | 32.248 | 19.751 | 29.839 | 27.778 | 29.802 | 28.736 |
| Breast LM | 9 | 25.381 | 32.310 | 19.668 | 30.266 | 27.705 | 29.566 | 29.577 |
| Breast LM | 10 | 26.174 | 32.970 | 20.036 | 32.305 | 28.691 | 30.722 | 29.632 |
| Breast LM | 10 | 26.062 | 32.313 | 19.916 | 32.080 | 28.712 | 31.071 | 29.973 |
| Breast LM | 11 | 29.221 | 35.174 | 24.557 | 36.691 | 33.055 | 33.915 | 32.966 |
| Breast LM | 11 | 29.204 | 34.316 | 24.509 | 36.177 | 32.815 | 33.137 | 33.631 |
| Breast LM | 12 | 30.453 | UD | 27.958 | 33.654 | 30.871 | 33.833 | 31.953 |
| Breast LM | 12 | 30.371 | UD | 28.002 | 33.772 | 30.846 | 33.242 | 32.321 |
| Breast LM | 13 | 27.006 | 33.424 | 22.239 | 33.263 | 29.571 | 30.881 | 30.444 |
| Breast LM | 13 | 27.006 | 33.535 | 22.293 | 33.286 | 29.470 | 30.810 | 30.672 |
| Breast LM | 14 | 25.784 | 33.436 | 20.025 | 27.453 | 24.736 | 26.462 | 25.903 |
| Breast LM | 14 | 25.723 | 33.897 | 19.953 | 27.674 | 24.601 | 26.389 | 26.229 |
| Breast LM | 15 | 28.633 | 34.998 | 26.284 | 32.961 | 30.162 | 31.955 | 30.838 |
| Breast LM | 15 | 28.428 | 35.181 | 26.165 | 33.110 | 30.148 | 31.753 | 31.015 |
| Breast LM | 16 | 28.807 | 35.442 | 26.537 | 32.348 | 30.373 | 32.301 | 31.592 |
| Breast LM | 16 | 28.680 | 34.988 | 26.355 | 33.175 | 30.416 | 32.011 | 31.681 |
| Breast LM | 17 | 29.268 | 24.630 | 21.239 | 29.995 | 28.911 | 29.920 | 27.692 |
| Breast LM | 17 | 29.097 | 24.605 | 20.887 | 30.363 | 28.886 | 29.762 | 28.305 |
| Breast LM | 18 | 29.702 | 31.968 | 26.406 | 31.073 | 30.501 | 32.820 | 29.712 |
| Breast LM | 18 | 29.969 | 31.514 | 26.260 | 31.508 | 30.430 | 32.741 | 29.802 |
| Breast LM | 19 | 26.527 | 31.477 | 22.035 | 28.358 | 30.716 | 30.165 | 26.926 |
| Breast LM | 19 | 26.526 | 31.654 | 21.967 | 28.392 | 30.713 | 30.015 | 27.044 |
| Breast LM | 20 | 26.373 | 35.276 | 19.590 | 26.371 | 27.901 | 25.011 | 24.178 |
| Breast LM | 20 | 26.270 | 34.665 | 19.544 | 26.438 | 27.631 | 25.089 | 24.138 |
| Breast LM | 21 | 28.123 | 34.414 | 23.245 | 29.885 | 23.275 | 31.398 | 28.881 |
| Breast LM | 21 | 28.134 | 34.245 | 23.257 | 29.831 | 23.046 | 31.542 | 28.934 |
| Breast LM | 22 | 32.904 | UD | 29.293 | 34.773 | 34.715 | 36.438 | 33.616 |
| Breast LM | 22 | 33.028 | UD | 29.127 | 34.571 | 34.321 | 37.548 | 33.449 |
| Breast LM | 23 | 27.233 | 35.308 | 21.986 | 28.639 | 29.883 | 31.056 | 27.869 |
| Breast LM | 23 | 27.156 | 36.094 | 22.032 | 28.654 | 29.878 | 31.049 | 28.177 |
| Breast LM | 24 | 28.149 | 33.316 | 25.137 | 27.720 | 27.842 | 30.901 | 26.319 |
| Breast LM | 24 | 27.947 | 32.855 | 24.882 | 27.926 | 27.995 | 30.793 | 26.763 |
| Breast LM | 25 | 27.659 | 34.227 | 19.330 | 26.775 | 23.657 | 24.032 | 23.402 |
| Breast LM | 25 | 27.362 | 34.603 | 19.135 | 27.104 | 23.416 | 23.953 | 24.071 |
| Breast LM | 26 | 31.169 | UD | 25.420 | 28.289 | 25.468 | 30.137 | 26.360 |
| Breast LM | 26 | 30.721 | UD | 25.250 | 28.572 | 25.305 | 30.119 | 26.642 |

TABLE 2B-continued

|  |  | miRNA | | | | | | |
| --- | --- | --- | --- | --- | --- | --- | --- | --- |
| Type | # | 125b | 10b | 21 | 141 | 200a | 200b | 200c |
| Lung to Brain | 1 | 27.3027 | 31.5496 | 22.65115 | 25.3368 | 25.2186 | 28.9333 | 24.1757 |
| Lung to Brain | 1 | 27.2988 | 31.1058 | 23.05115 | 25.3807 | 25.1565 | 28.3453 | 23.8634 |
| Lung to Brain | 2 | 29.8443 | 34.8497 | 25.1519 | 32.1757 | 31.3363 | 34.9516 | 30.1594 |
| Lung to Brain | 2 | 29.7741 | 34.7253 | 24.5772 | 31.9565 | 31.6946 | 35.3302 | 29.1884 |
| Lung to Brain | 3 | 33.0843 | UD | 29.3511 | 34.3175 | 34.4514 | 37.0247 | 33.1313 |
| Lung to Brain | 3 | 33.5869 | UD | 29.4506 | 34.7511 | 34.8228 | 36.7855 | 32.3656 |
| Lung to Brain | 4 | 32.6941 | UD | 28.2911 | 33.9836 | 31.5455 | 33.2976 | 30.4481 |
| Lung to Brain | 4 | 32.6056 | UD | 27.1608 | 32.7802 | 31.2428 | 33.0444 | 30.4042 |
| Lung to Brain | 5 | 30.2049 | 34.8968 | 24.7768 | 30.4436 | 28.4256 | 30.2405 | 27.5537 |
| Lung to Brain | 5 | 29.5105 | 34.7725 | 24.0629 | 30.5538 | 28.1955 | 29.9892 | 27.1272 |
| Lung to Brain | 6 | 32.5851 | 36.6255 | 29.7253 | 35.4127 | 33.7658 | 35.5324 | 30.491 |
| Lung to Brain | 6 | 32.7851 | 37.4443 | 29.7184 | 35.1166 | 33.1176 | 35.0508 | 31.0042 |
| Lung to Brain | 7 | 29.261 | 33.4991 | 24.232 | 28.9268 | 28.5605 | 30.46 | 27.6959 |
| Lung to Brain | 7 | 28.4163 | 33.0663 | 23.8848 | 28.9189 | 28.312 | 30.706 | 27.9061 |
| Lung to Brain | 8 | 30.4814 | 34.687 | 22.3076 | 28.6553 | 27.6452 | 30.3316 | 29.4116 |
| Lung to Brain | 8 | 30.776 | 35.2047 | 21.9802 | 29.0701 | 27.6333 | 29.272 | 28.661 |
| Lung to Brain | 9 | 30.2956 | 34.349 | 26.8941 | 30.8863 | 29.4441 | 31.3527 | 31.2236 |
| Lung to Brain | 9 | 29.9115 | 33.5384 | 27.4941 | 31.091 | 29.5607 | 31.5945 | 29.1472 |
| Lung to Brain | 10 | 29.1638 | 35.0255 | 22.6924 | 29.9554 | 32.817 | 31.0666 | 27.3901 |
| Lung to Brain | 10 | 29.4353 | 34.4966 | 23.1541 | 30.097 | 32.9107 | 31.0331 | 27.2599 |
| Lung to Brain | 11 | 27.4463 | 33.4652 | 21.1578 | 26.99988 | 25.7732 | 28.9661 | 25.0689 |
| Lung to Brain | 11 | 27.3261 | 34.1371 | 20.9667 | 26.3149 | 25.4019 | 28.0832 | 24.8732 |
| Lung to Brain | 12 | 32.8667 | UD | 30.8165 | UD | UD | UD | 38.2814 |
| Lung to Brain | 12 | 32.2667 | UD | 30.3494 | UD | UD | UD | 37.08 |
| Lung to Brain | 13 | 34.1699 | UD | 24.4215 | 30.4942 | 29.2874 | 31.5813 | 31.9309 |
| Lung to Brain | 13 | 34.2134 | UD | 24.2206 | 30.0906 | 29.0842 | 31.5813 | 32.2984 |
| Lung to Brain | 14 | 29.293 | 34.571 | 24.394 | 30.789 | 29.544 | 33.057 | 28.864 |
| Lung to Brain | 14 | 29.009 | 35.563 | 24.532 | 30.838 | 29.377 | 32.956 | 28.902 |
| Lung to Brain | 15 | 28.914 | 34.550 | 22.560 | 29.644 | 28.600 | 30.866 | 27.167 |
| Lung to Brain | 15 | 28.707 | 34.495 | 22.627 | 29.678 | 28.693 | 30.347 | 27.103 |
| Lung to Brain | 16 | 26.601 | 31.991 | 22.155 | 27.351 | 26.558 | 28.982 | 26.586 |
| Lung to Brain | 16 | 26.458 | 32.220 | 22.243 | 27.760 | 26.265 | 28.980 | 27.004 |
| Lung to Brain | 17 | 30.365 | 35.322 | 22.837 | 28.904 | 28.364 | 30.994 | 27.650 |
| Lung to Brain | 17 | 30.368 | 35.505 | 22.640 | 28.751 | 27.744 | 31.052 | 27.517 |
| Lung to Brain | 18 | 30.310 | 35.762 | 29.548 | 34.882 | 35.961 | 39.607 | 33.730 |
| Lung to Brain | 18 | 30.162 | 37.352 | 29.501 | 35.203 | 35.808 | 38.411 | 34.555 |
| Lung to Brain | 19 | 29.630 | 32.016 | 24.964 | 27.431 | 28.617 | 30.526 | 27.507 |
| Lung to Brain | 19 | 29.594 | 31.720 | 24.962 | 27.681 | 28.632 | 30.398 | 27.934 |
| Lung to Brain | 20 | 28.500 | UD | 23.147 | 26.762 | 28.607 | 29.801 | 25.805 |
| Lung to Brain | 20 | 28.472 | UD | 23.183 | 26.857 | 28.429 | 29.778 | 25.829 |
| Lung to Brain | 21 | 26.383 | 33.937 | 21.266 | 29.484 | 30.964 | 31.936 | 28.164 |
| Lung to Brain | 21 | 26.398 | 33.081 | 21.299 | 29.664 | 30.766 | 31.886 | 28.331 |
| Lung to Brain | 22 | 27.589 | 36.414 | 24.198 | 31.107 | 33.120 | 35.063 | 30.855 |
| Lung to Brain | 22 | 27.681 | 36.387 | 24.163 | 31.499 | 32.544 | 34.379 | 30.925 |
| Lung to Brain | 23 | 27.335 | 33.311 | 20.275 | 26.183 | 27.803 | 29.310 | 26.190 |
| Lung to Brain | 23 | 27.203 | 32.897 | 20.198 | 26.497 | 27.698 | 29.155 | 26.421 |
| Lung to Brain | 24 | 31.188 | 33.761 | 24.351 | 30.843 | 31.061 | 32.678 | 30.078 |
| Lung to Brain | 24 | 31.066 | 34.498 | 24.576 | 31.006 | 30.770 | 32.639 | 29.865 |
| Lung to Brain | 25 | 25.438 | 33.677 | 22.276 | 27.030 | 26.485 | 28.167 | 25.754 |
| Lung to Brain | 25 | 25.257 | 32.734 | 22.333 | 27.055 | 26.320 | 28.058 | 25.845 |
| Lung to Brain | 26 | 27.957 | 35.622 | 26.272 | 30.664 | 29.900 | 32.145 | 28.598 |
| Lung to Brain | 26 | 27.770 | 35.349 | 25.912 | 30.721 | 29.989 | 32.029 | 28.710 |
| Lung to Brain | 27 | 27.791 | 35.924 | 23.314 | 30.597 | 29.887 | 31.737 | 29.783 |
| Lung to Brain | 27 | 27.719 | 36.972 | 22.870 | 31.188 | 29.900 | 32.049 | 30.955 |
| Lung to Brain | 28 | 27.600 | 34.338 | 22.529 | 26.370 | 28.088 | 31.174 | 26.558 |
| Lung to Brain | 28 | 27.498 | 34.905 | 21.968 | 26.742 | 27.800 | 31.009 | 26.244 |
| Lung LM | 1 | 28.652 | 30.282 | 22.137 | 25.738 | 24.665 | 27.190 | 25.600 |
| Lung LM | 1 | 28.606 | 30.400 | 21.843 | 26.250 | 24.557 | 27.097 | 25.948 |
| Lung LM | 2 | 27.795 | 33.788 | 24.948 | 39.425 | 36.261 | 37.184 | 37.034 |
| Lung LM | 2 | 27.934 | 32.653 | 24.846 | 38.606 | 36.606 | 37.702 | 36.898 |
| Lung LM | 3 | 27.478 | 37.812 | 31.801 | 29.974 | 29.569 | 31.303 | 28.059 |
| Lung LM | 3 | 27.310 | 37.200 | 31.664 | 30.034 | 29.446 | 31.181 | 28.566 |
| Lung LM | 4 | 27.588 | 32.726 | 19.656 | 24.357 | 24.419 | 27.413 | 24.179 |
| Lung LM | 4 | 27.627 | 32.723 | 19.472 | 24.376 | 24.369 | 27.213 | 24.289 |

UD = Undetermined

Figure 7A:
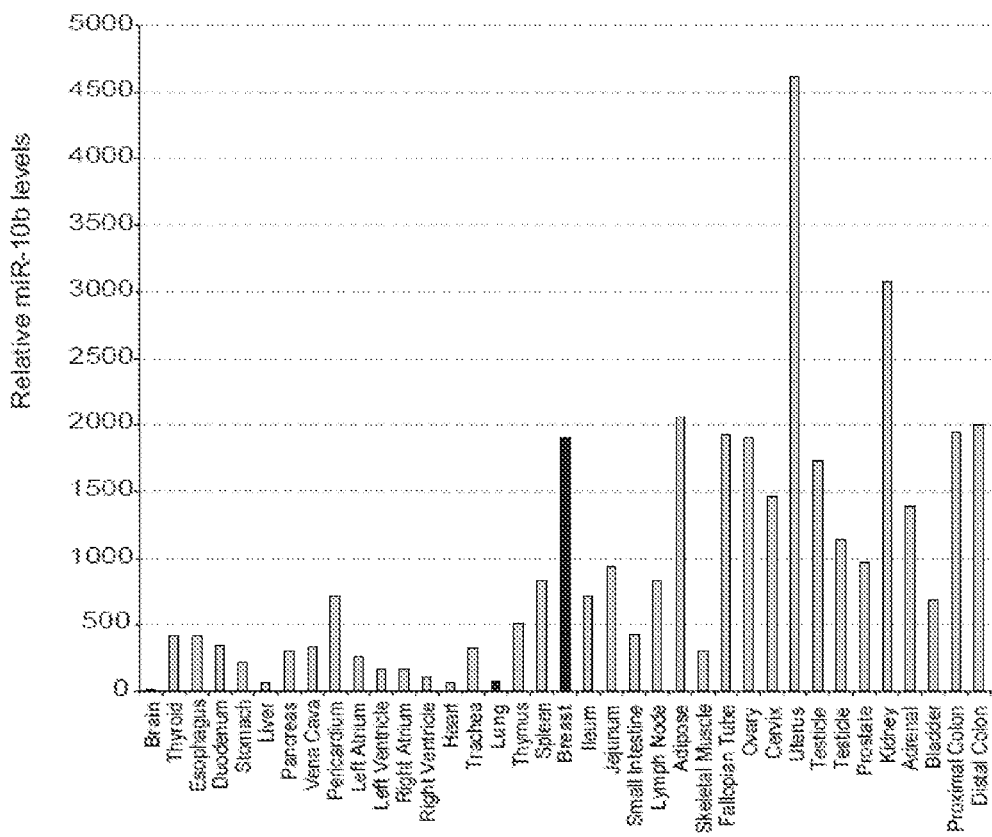
FIGS. 7A-B are bar graphs showing miR-10b expression in different human tissues. (7A) The normalized data on miR-10b expression in various human tissues were obtained from qRT-PCR based profiling (Liang, 2007). miR-10b levels were calculated relative to miR-10b expression in brain, which was set as one unit. (7B) The data on miR-10b expression in normal human tissues and corresponding carcinomas were obtained from profiling based on hybridization arrays (Lu, 2005), Gene Expression Omnibus (GEO) accession number GSE2564. Normalized miR-10b signals were plotted relative to miR-10b level in brain, which was set as one unit.
Figure 7B:
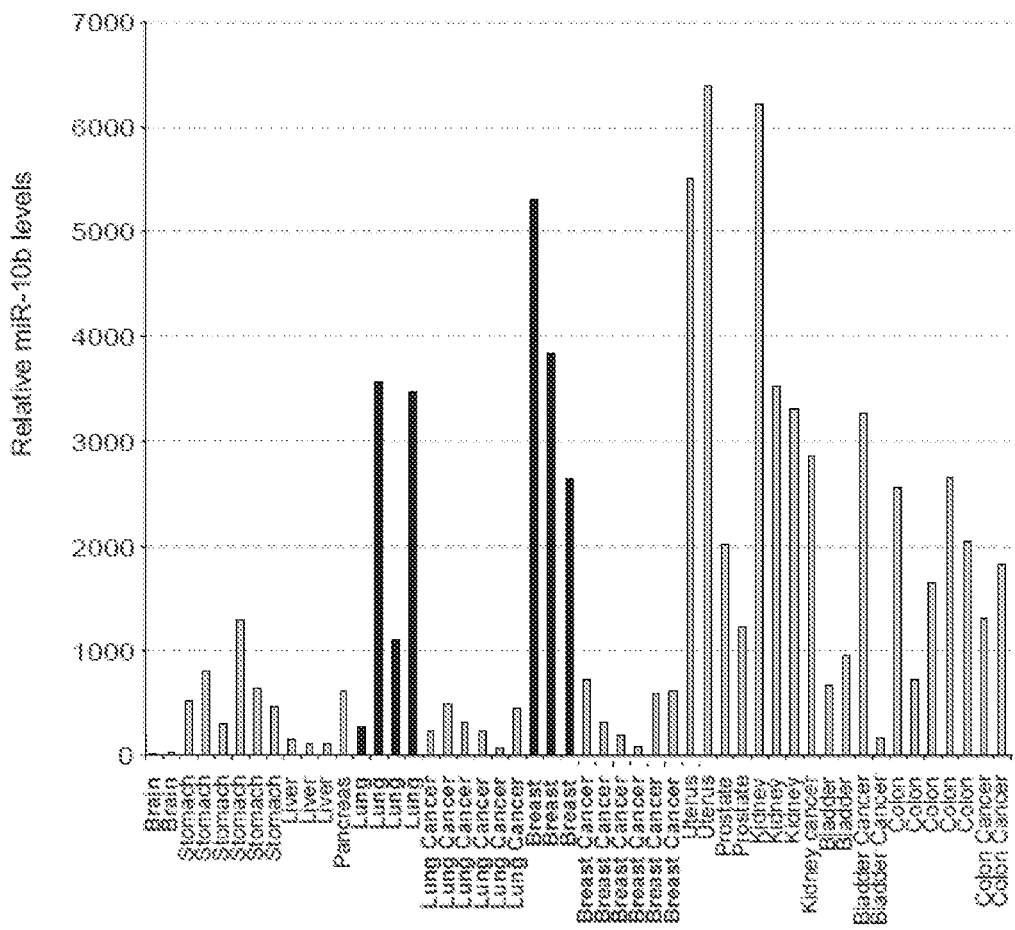

Example 2 miR-200 Family in the CSF is Indicative of Brain Metastasis miR-10b is expressed in most extracranial tissues[21,22] (FIGS. 7A-B), and abundant in blood serum[23]. However, it is not expressed in brain and not detectable in CSF of non-cancer patients. Therefore, miR-10b and other miRNAs seem unlikely to pass the blood-brain barrier under non-neoplastic conditions, and miRNAs in CSF might therefore reflect a unique miRNA signature of brain. On the other hand, miR-10b is highly expressed in breast and lung tissues, and its presence in the CSF of lung and breast cancer patients with CNS metastasis indicates that metastatic cells bring their signature miRNAs to the CSF. Based on these data, other miRNA CSF biomarkers were sought that could enable discrimination between GBM and metastatic brain tumors. Such miRNAs should be highly expressed in a primary carcinoma or tissues of its origin (e.g. lung or breast) but not in brain or GBM.

Figure 2A:
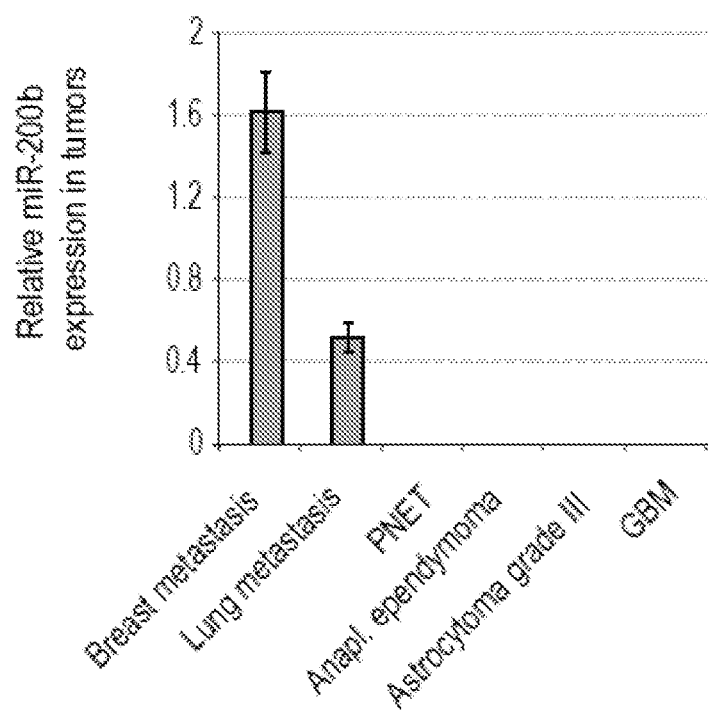
FIGS. 2A-F show the results of detection of miRNAs of miR-200 family in metastatic brain cancer patients. (2A) miR-200b expression levels were examined by qRT-PCR in various primary and metastatic brain tumor tissue specimens and normalized to ubiquitously expressed miR-125b. Error bars indicate standard errors between technical duplicates. PNET: primitive neuroectodermal brain tumor. MiR-200a (2B), miR-200b (2C), miR-200c (2D) and miR-141 (2E) levels were examined by qRT-PCR in CSF samples of neurological patients, and the relative values are demonstrated for individual patients. Differences between group means that reached statistical significance as determined by non-parametric Wilcoxon Signed Rank test are indicated with asterisks: (*) $p<0.05$, () $p<0.001$, (*) $p<0.0001$. Corresponding values normalized to miR-125b are presented in Suppl.
Figure 2B:
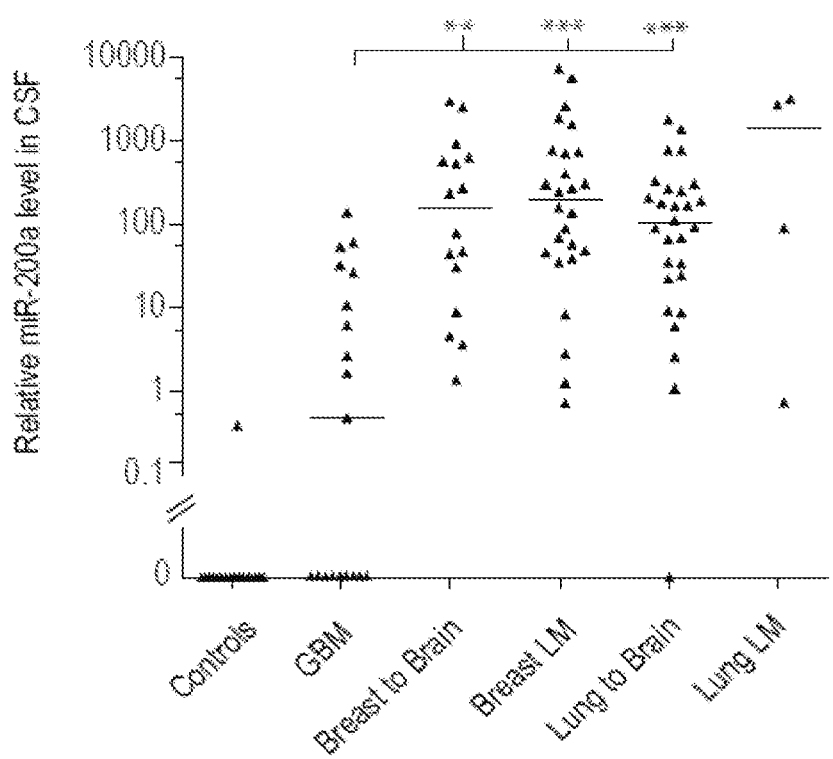
Figure 2C:
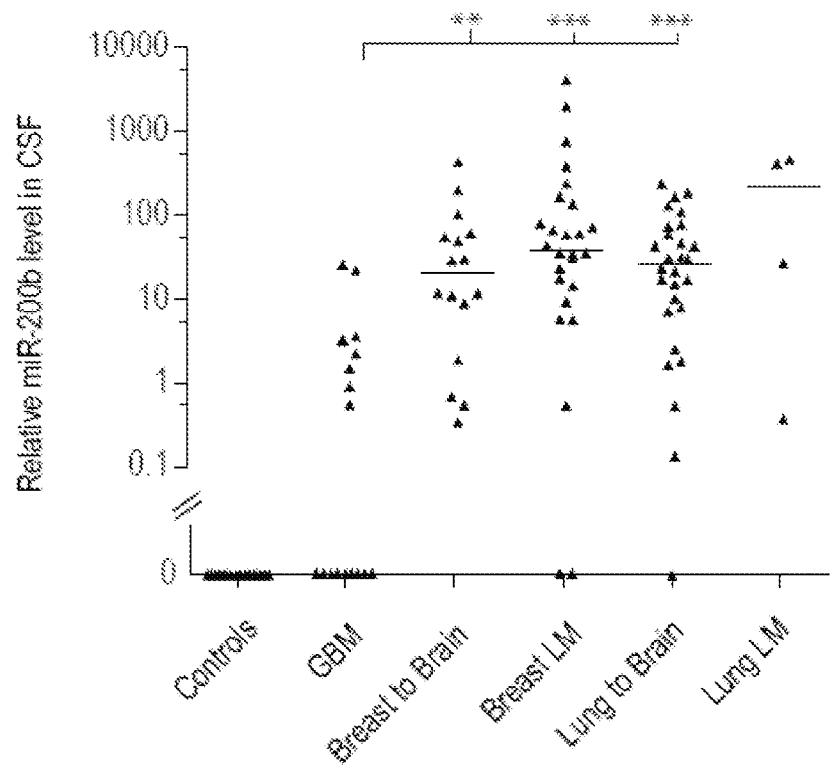
Figure 2D:
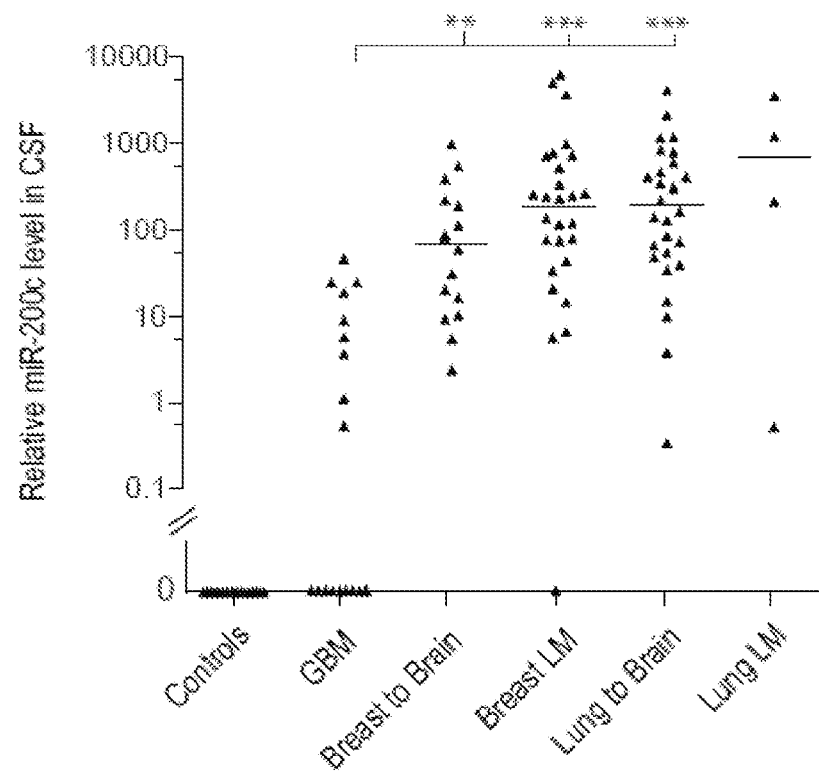
Figure 2E:
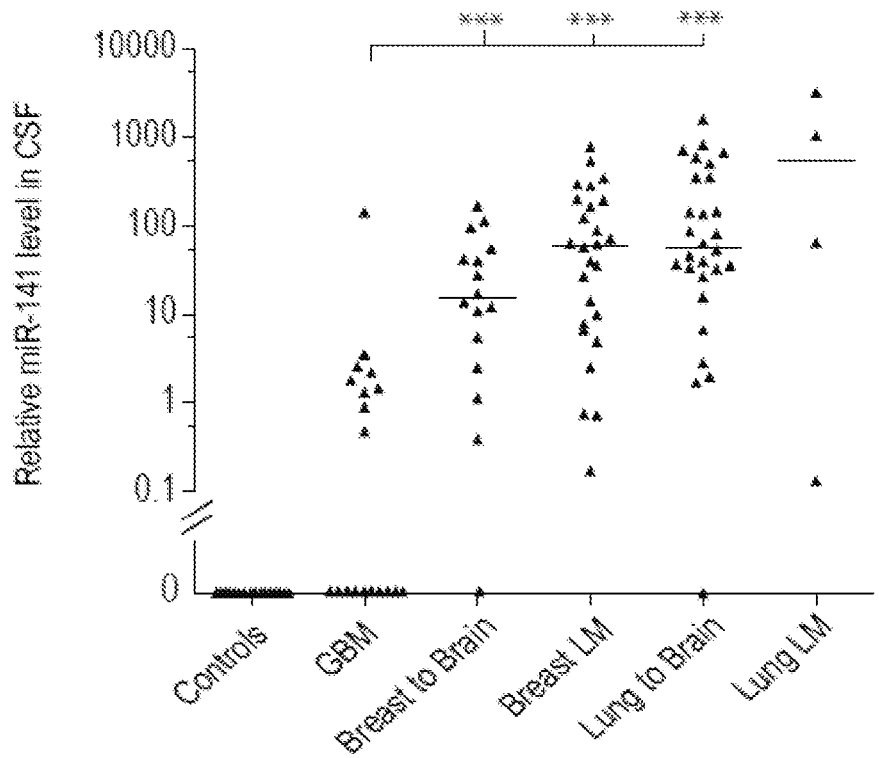
Figure 8A:
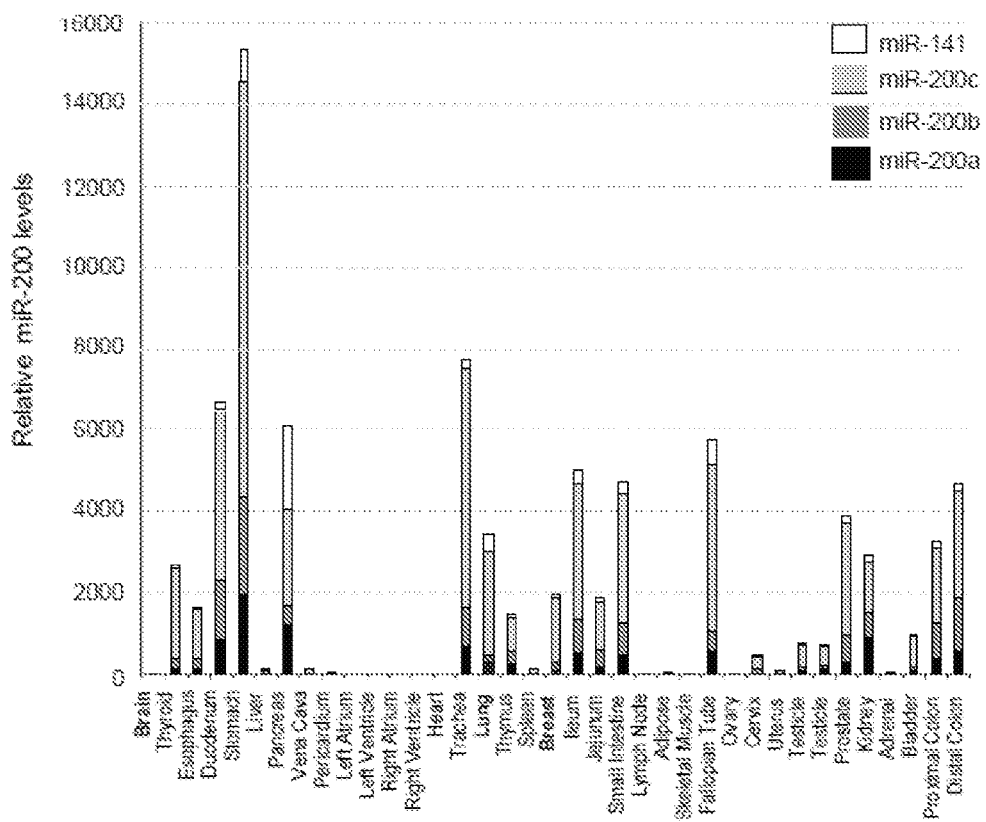
FIGS. 8A-B are bar graphs showing miRNA-200 family in different human tissues. (8A) The normalized data on miR-200a, -200b, 200c and miR-141 expression in human tissues were obtained from qRT-PCR based profiling (Liang, 2007). miRNA levels were calculated relative to corresponding miRNA expression levels in brain, which were set as one unit. (8B) The data on miR-200 family expression in normal human tissues and corresponding carcinomas were obtained from profiling based on hybridization arrays (Lu, 2005); Gene Expression Omnibus (GEO) accession number GSE2564. Normalized signals for specific miRNAs were plotted relative to corresponding miRNA levels in brain, which were set as one unit.
Figure 8B:
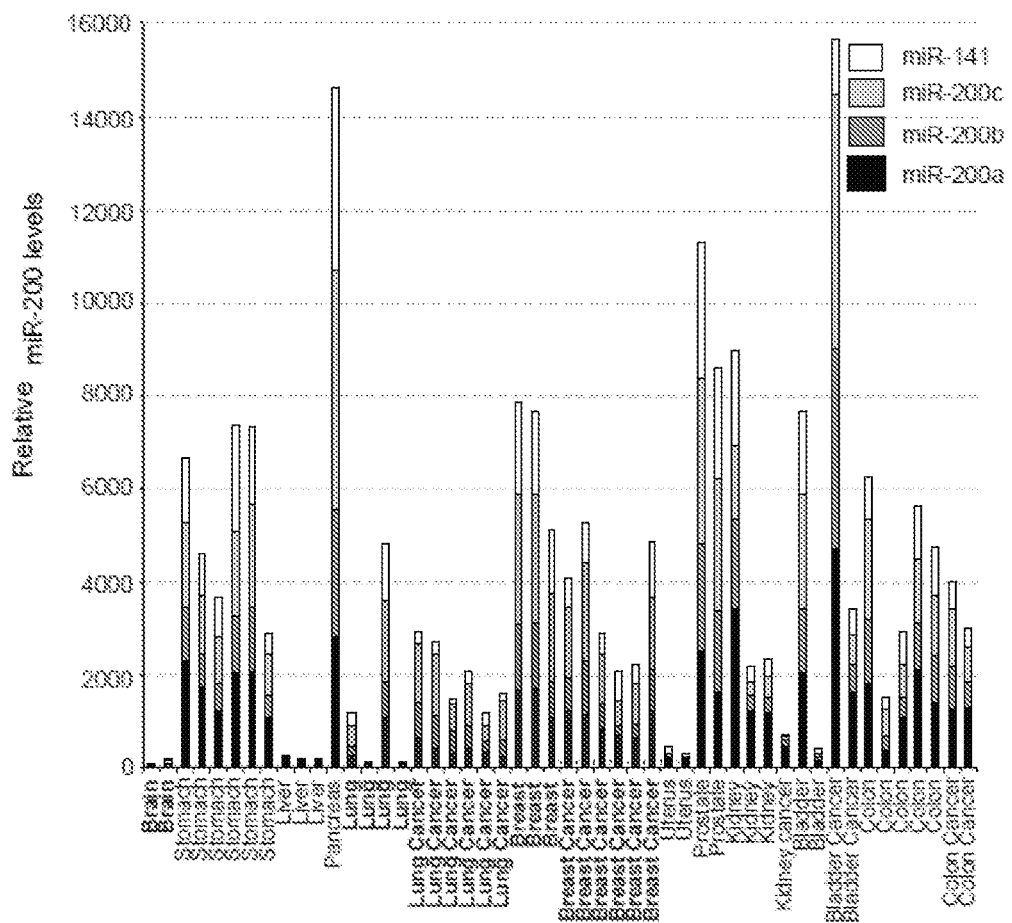

According to miRNA profiling across different tissues, miRNAs of miR-200 family are good candidates fulfilling this criteria. All members of this family are highly expressed in lung and breast tissues and epithelial cancers, including lung and breast carcinomas, but are barely detectable in brain[22,24], and FIGS. 8A-B). On the other hand the miR-200 family, unlike miR-10b, is not expressed in GBM and other primary brain tumors, making it a putative biomarker for metastatic brain cancer (FIG. 2A).

To explore a potential of miRNA-200 for distinguishing between GBM and metastatic brain cancer, the levels of four miR-200 family members, miR-200a, miR-200b, miR-200c and miR-141, were assessed in CSF of control, GBM and metastatic brain cancer patients. Remarkably, all four miR-NAs were highly expressed in the majority of CSF samples collected from the patients with brain and leptomeningial metastasis, but not in the control or GBM cases (FIG. 2B-E). These data suggest miR-200 levels might be used for discriminating between primary brain cancer and brain metastasis.

Figure 2F:
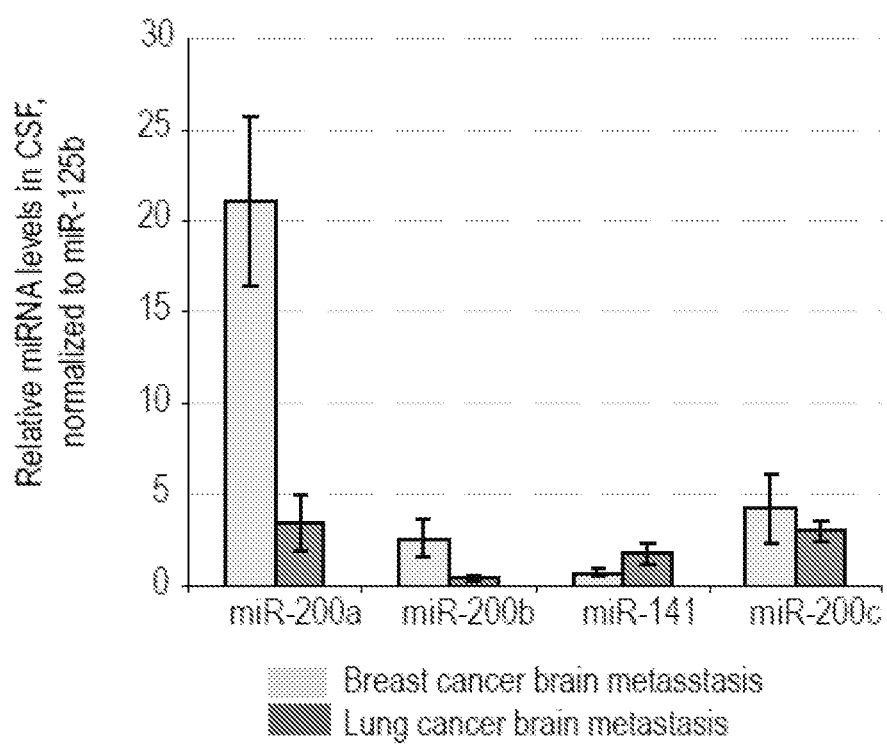
Figure 9:
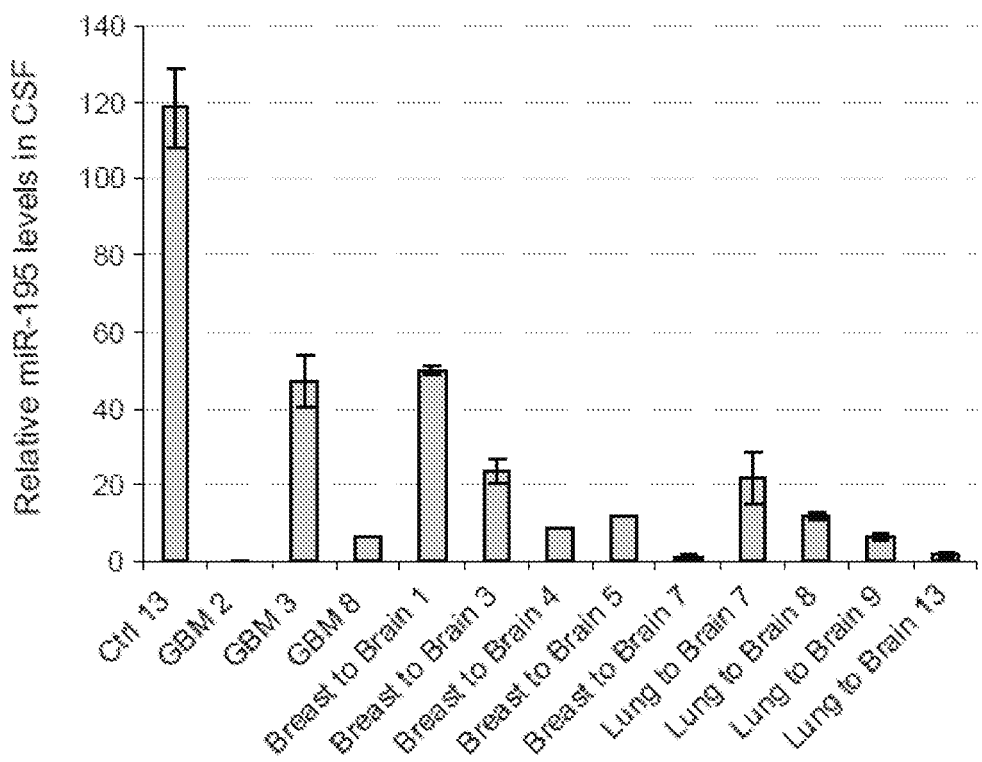
FIG. 9. miR-195 levels in CSF of randomly selected patients with GBM, metastatic brain cancers and non-neoplastic controls. miR-195 levels in CSF samples were determined by qRT-PCR reaction. Relative miRNA levels were quantified by ΔCt method as described. Error bars represent standard error of mean between technical duplicates.

In attempt to discriminate between metastasis from breast vs. lung cancer, miR-195 levels were assessed in several randomly selected CSF samples, since circulating miR-195 was proposed as a differential biomarker of breast vs. lung cancer[25]. However, no significant differences were found in miR-195 levels in CSF of breast and lung cancer metastasis patients (FIG. 9). Another miRNA, miR-1 is expressed at higher levels in breast versus lung tissue according to miRNA expression profiles[22] but miR-1 was undetectable in CSF of both breast and lung cancer cohorts of patients. Breast and lung carcinomas express strikingly similar miRNA repertoire[21]. However, there were significantly higher amounts of miR-200a and miR-200b (two miRNAs encoded as a cluster at chromosome 1p36.33) in CSF of the patients with breast cancer relative to lung cancer, while CSF levels of miR-141 and -200c (co-encoded at chromosome 12p13.31) were similar in breast and lung cancer cases (FIG. 2F). These data suggest that the ratios between miRNAs of two different miR-200 genomic clusters in CSF may be informative for discrimination between brain metastasis from breast versus lung cancer.

Example 3

Figure 3A:
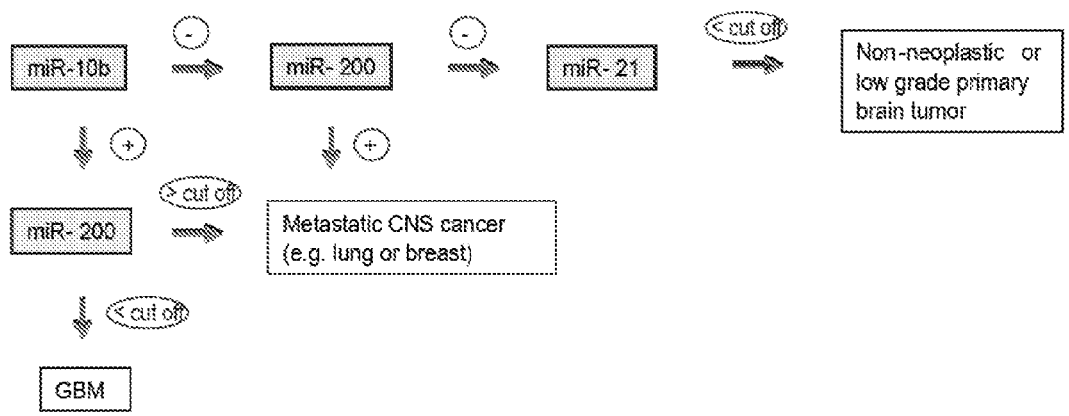
FIG. 3A is an exemplary diagnostic decision tree showing a method of classification of brain cancer patients based on CSF miRNA biomarkers (miR-10b, -21, and -200).

Computational Classification of High-Grade Brain Malignancies Based on CSF miRNA Profiling The relationships discovered between the miRNA CSF levels and diagnostic outcomes are illustrated by a simple diagnostic decision tree (FIG. 3A). The next experiments tested whether the samples can be classified into classes more accurately (non-neoplastic control vs. GBM vs. metastasis) using a "machine-learning technique" based on Support Vector Machine (SVM) concept. This technique was previously applied to a wide range of biological problems, including mRNA and miRNA expression data analysis in cancers[26-28].

Various SVM algorithms were applied for classification of the samples. In one case (GBM vs. metastasis classification) a very simple linear classifier provides discrimination with about 95% accuracy. The levels of two miRNAs, miR-200a and miR-125b were used in this case as independent variables, and a linear function of these two Ct levels employed as a classifier with the coefficients calculated in the process of the classifier training.

Another case that allows for a similar interpretation is the classification of GBM and brain metastasis versus non-neoplastic controls. In that case a linear classifier was constructed that uses Ct levels of three miRNAs: miR-10b, miR-200a and miR-125b as features. Accordingly, a two-dimensional plane in the space spawned by the levels of these three miRNAs separated the space into two domains.

Linear algorithms provided satisfactory classification for GBM v Metastasis (using the formula 0.3364*miR-125b+0.0808*miR-10b+0.4578*miR-21+−0.0871*miR-141+0.001*miR-200a+0.0213*miR-200b+−0.3419*miR-200c−7.2516); GBM and metastasis versus non-neoplastic (0.0003*miR-125b+−0.0021*miR-10b+−0.0002*miR-21+0*miR-141+0*miR-200a+0*miR-200b+−0.0021*miR-200c+3.1536); GBM versus non-neoplastic (0.0002*miR-125b+0.0021*miR-10b+−0.0001*miR-21+0*miR-141+0*miR-200a+0*miR-200b+0*miR-200c−1.0849); Metastases versus non-neoplastic (0*miR-125b+0*miR-10b+0*miR-21+0*miR-141+0*miR-200a+0*miR-200b+0.0021*miR-200c−1.0744); GBM versus non-GBM (all others) (0.2468*miR-125b+0.1816*miR-10b+0.107*miR-21+0.0007*miR-141+0.0003*miR-200a+−0.0032*miR-200b+−0.1817*miR-200c−7.7752); Metastasis versus non-metastasis (all others) (0.3348*miR-125b+0.0838*miR-10b+0.4619*miR-21+−0.0902*miR-141+0.001*miR-200a+0.0284*miR-200b+−0.3482*miR-200c−7.3231); Breast versus lung (0.1592*miR-125b+−0.0003*miR-10b+0.0381*miR-21+−0.5325*miR-141+0.5346*miR-200a+−0.0014*miR-200b+−0.1282*miR-200c−1.0529). In each case, a negative result puts the sample into the first class, and a positive result puts the sample into the second class.

Similarly, various SVM classifiers were tested and the RBF kernel provided good separation between all classes of samples. The best classification accuracy was achieved using the levels of seven miRNAs: miR-10b, miR-21, miR-125b, miR-141, miR-200a, miR-200b, and miR-200c as independent variables.

This analysis revealed that different types of cancer are distinguished from each other as well as from non-neoplastic control with the average cross-validation accuracy of about 90% (Table 2A). That means that the SVM incorrectly predicted the class of about one often previously unseen samples. This analysis suggests a possibility of computational differential diagnostics of brain cancers using miRNA profiling.

Example 4

Figure 3B:
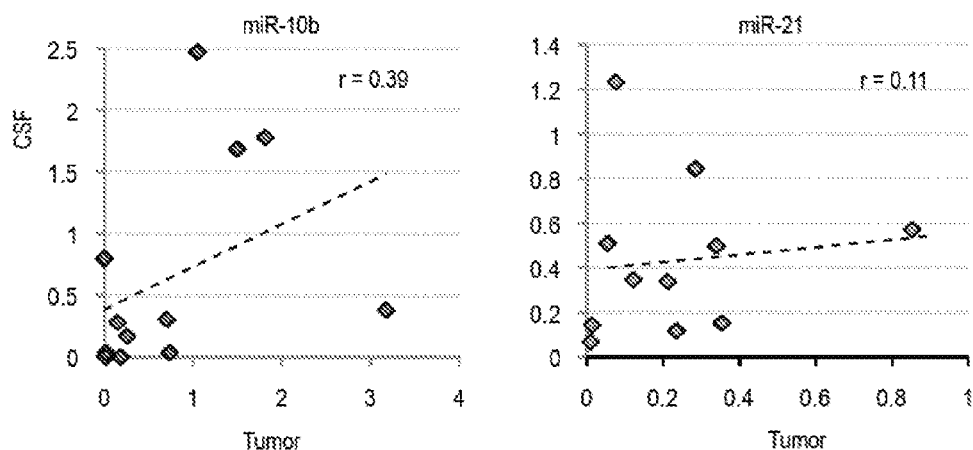
FIG. 3B is a pair of graphs showing the correlation of miR-10b and miR-21 levels between brain tumors and matching CSF samples collected from the same patients. The Pearson coefficients (r) of linear regression between two data sets were calculated for each miRNA.

The Origin of miRNA in CSF miRNAs detected in the CSF of brain cancer patients may originate from brain tumor cells, from surrounding brain tissues or from extracranial tissues due to the blood-brain barrier disruption associated with tumor growth. To discriminate between these possibilities miR-10b and miR-21 expression levels were determined in tumor biopsies obtained during brain surgery and corresponding CSF samples from the same patients. A positive correlation was observed between miR-10b expression level in the brain tumor and corresponding CSF specimens, and no such correlation was observed for miR-21 (FIG. 3B). Of note, miR-10b is expressed in tumors but not in normal brain tissues, while miR-21 is elevated in tumors but is also present in normal brain[14,16]. Taking these expression patterns into account, the data suggest that miRNA composition of the CSF is established by tumor cells as well as by the cells of surrounding brain tissues.

Example 5 miRNAs in CSF of Brain Cancer Patients as Markers of Disease Activity

Figure 10A:
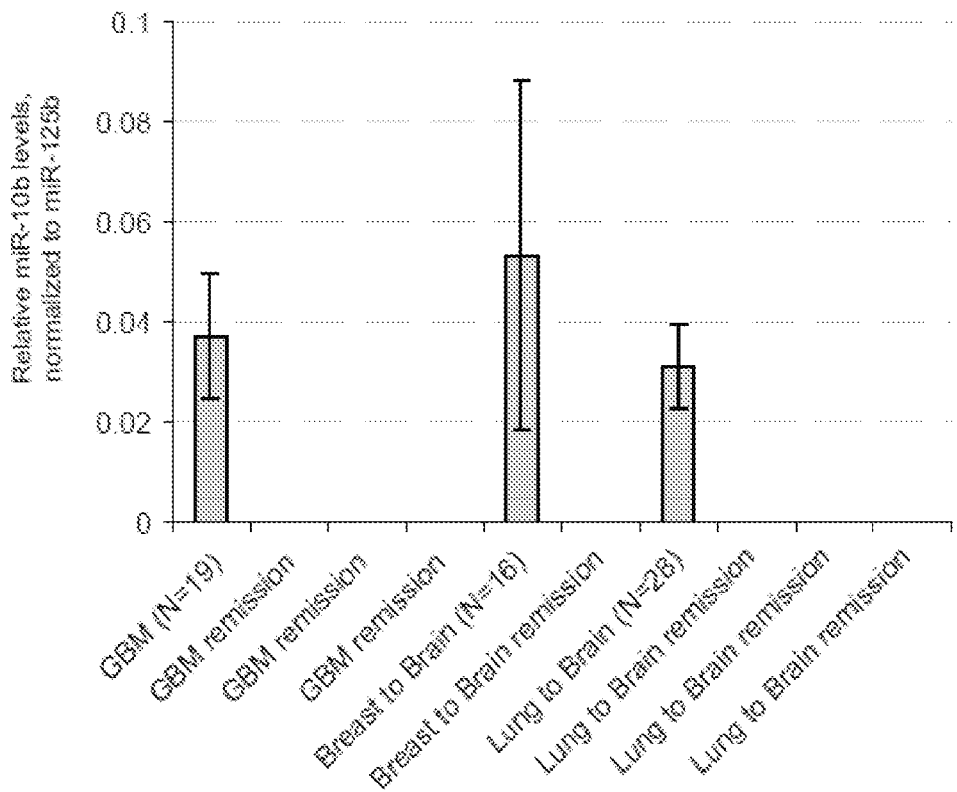
FIGS. 10A-F are graphs showing miRNA levels in CSF of patients with GBM and metastatic brain cancers remissions. The levels of (10A) miR-10b, (10B) miR-21, (10C) miR-200a, (10D) miR-200b, (10E) miR-200c and (10F) miR-141 were determined in CSF by qRT-PCR reaction. Relative miRNA levels were quantified by ΔCt method and normalized to miR-125b as described in Materials and methods. Average miRNA levels are presented for each group of cancer patients and individual miRNA levels are presented for patients with cancer remissions. Error bars represent standard error of mean within groups of patients.
Figure 10B:
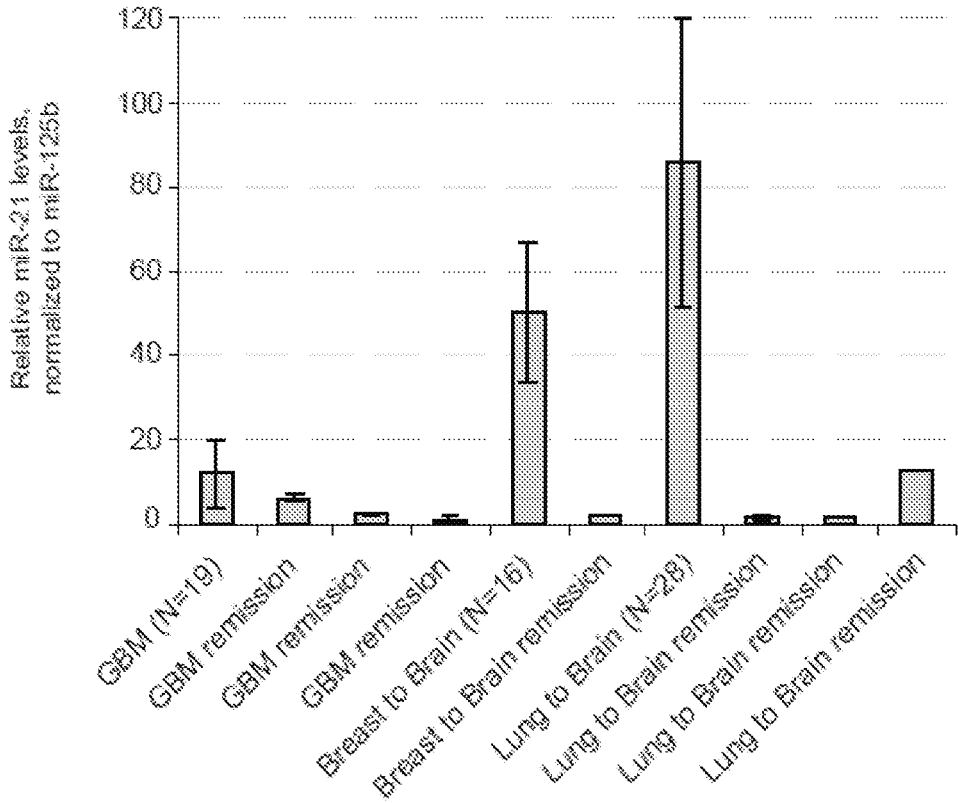
Figure 10C:
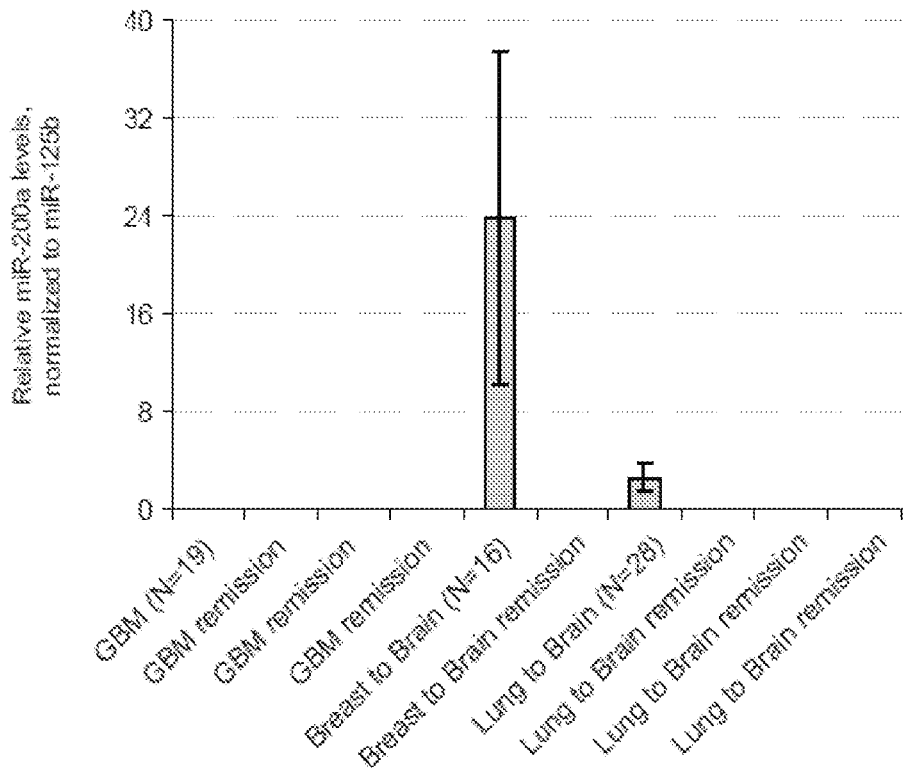
Figure 10D:
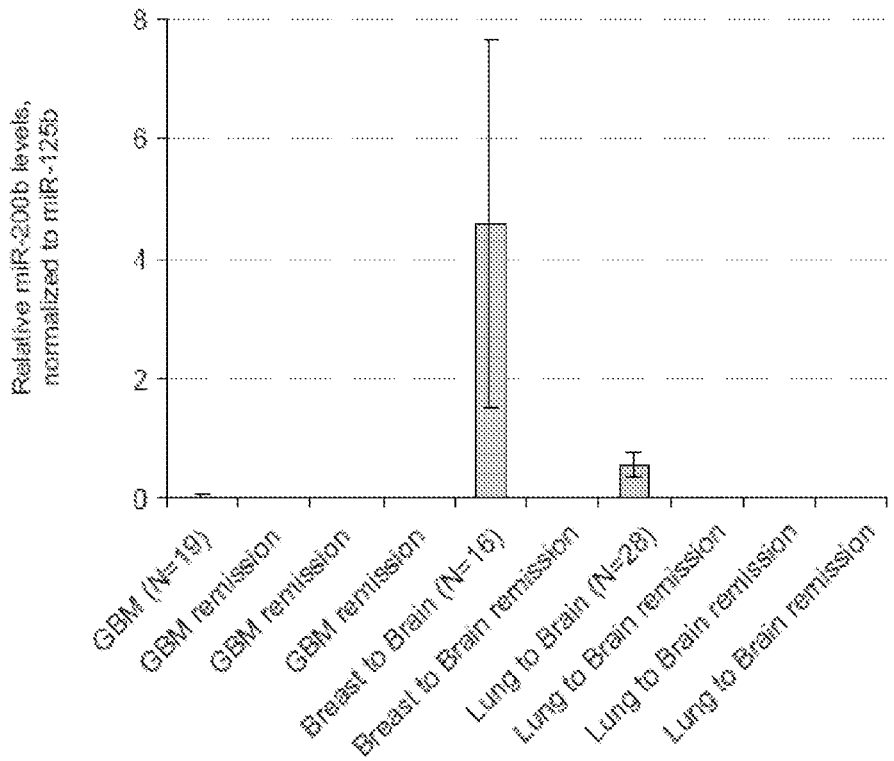
Figure 10E:
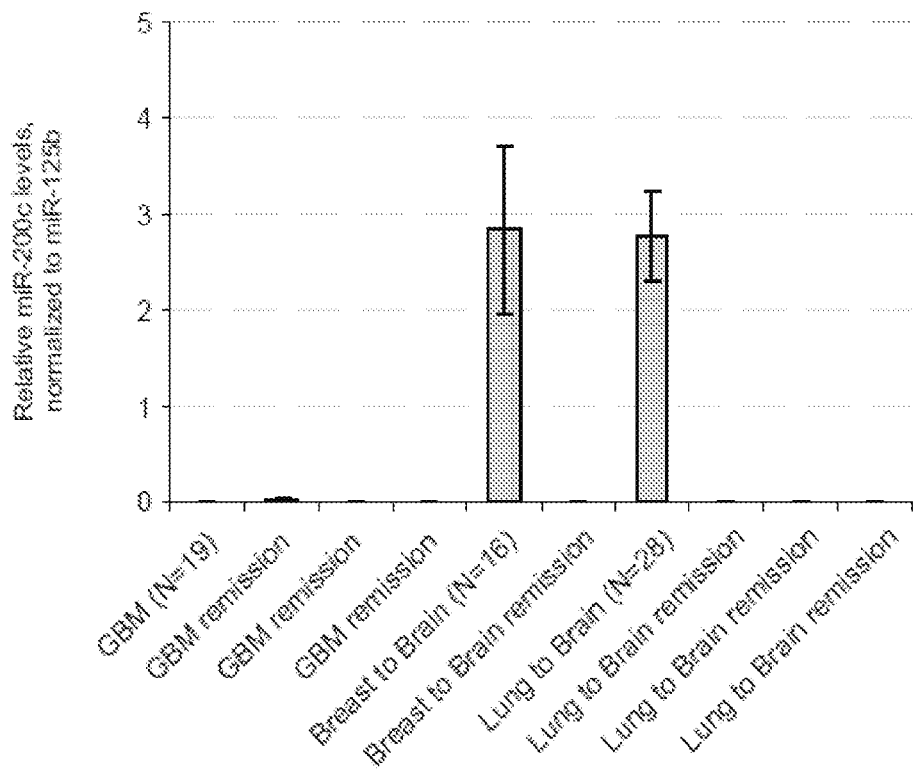
Figure 10F:
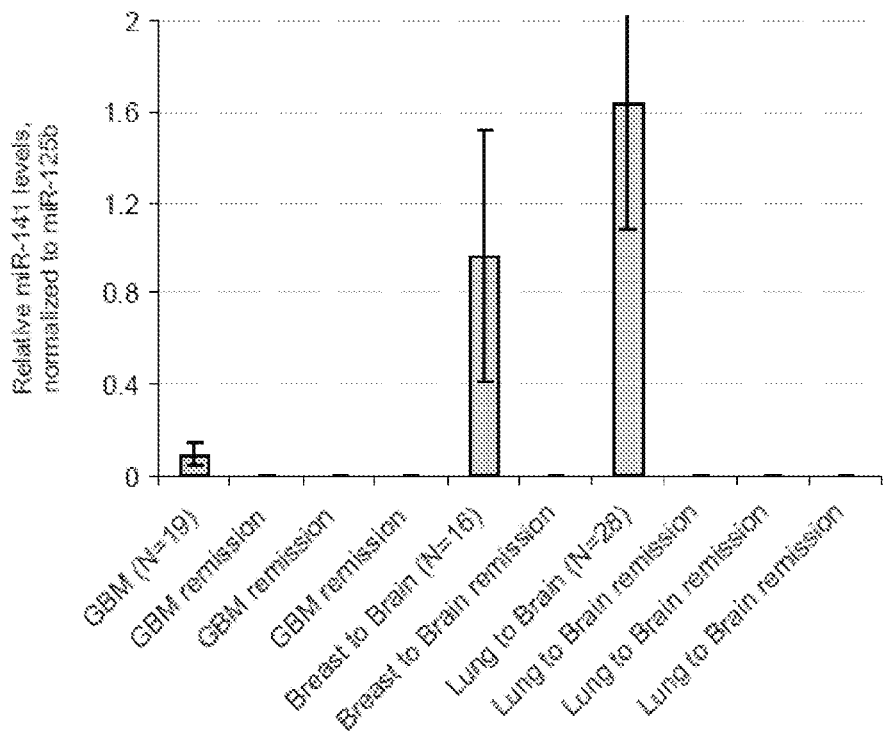

To examine whether CSF levels of miRNAs reflect a disease status/activity, miRNA was studied in CSF of active GBM and metastatic brain cancer versus tumor remission cases. The disease was considered in remission if, following treatment, there were no evidence of tumor mass detected by MRI and CSF cytological analysis was negative. Neither miR-10b nor miR-200 family members were detected after 40 cycles of qRT-PCR reaction in CSF samples in any of remission cases (Table 3, FIGS. 10A-F). MiR-21 levels were significantly lower in cancer remission cases as compared to active GBM and metastatic brain cancer cases before treatment (FIG. 10B). These data suggest that miRNAs analyzed in this study may reflect the activity of brain tumors.

Figure 4A:
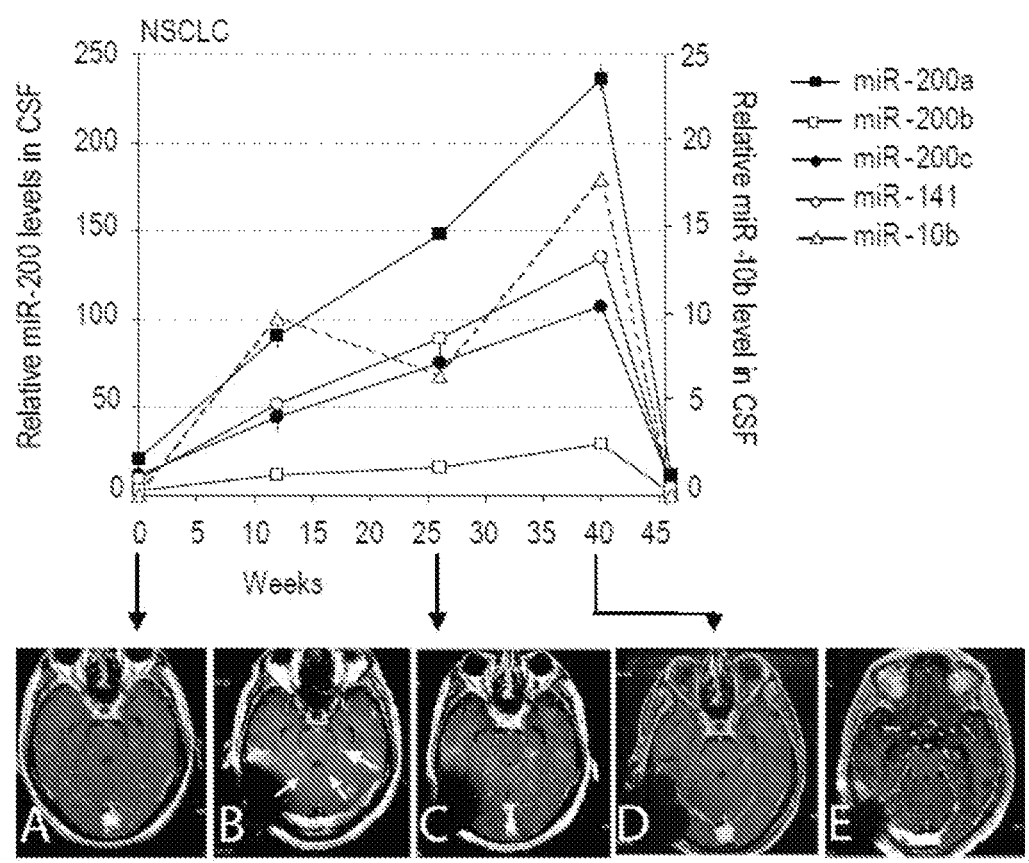
FIGS. 4A-C show CSF levels of miRNA markers in metastatic lung cancer and GBM patients during treatment with erlotinib. miRNAs levels were examined by qRT-PCR in CSF samples of lung cancer patients (Patients A, C) and GBM patient (Patient B) during the time course of erlotinib treatment. The disease progression and the drug response were concomitantly monitored by MRI, as following. For Patient A (shown in FIG. 4A): serial axial post-gadolinium MRIs of lung cancer patient's brain during course of progression of disease and stability and improvement on MRI with escalating doses of erlotinib. A: time 0 weeks while patient on erlotinib, there is no leptomeningeal and parenchymal enhancement and CSF cytology was negative; B: 3 weeks progression on erlotinib 150 mg daily dosing with new cerebellar leptomeningeal enhancement (small arrows) and nodule (large arrow), erlotinib increased to 600 mg every 4 days at 9 weeks; C: 29 weeks on showing stable leptomeningeal enhancement and nodule; D-40 weeks showing reduction in leptomeningeal enhancement and nodule, erlotinib increased to 900 mg every 4 days at 41 weeks; E: 64 weeks after 6 cycles of chemotherapy with carboplatinum and pemetrexed due to lung cancer progression showing further reduction in leptomeningeal enhancement and nodule has disappeared. For Patient B (shown in FIG. 4B): A: time 2 weeks for patient with GBM with predominant mass effect and enhancement felt to be radiation changes rather than tumor based on MRI spectroscopy and PET scan on erlotinib at 600 mg every 4 days; B: 26 weeks on treatment showing progression on MRI with new lesion (arrow) concerning for tumor; C: 27 weeks on treatment showing hypermetabolic area (arrow) on PET consistent with tumor and biopsy confirmed. For Patient C (shown in FIG. 4C): had inadequate treatment due to functional status and rapidly progressed over a few weeks, which was reflected by an increase in levels of miR-200 family members in a short interval.
Figure 4B:
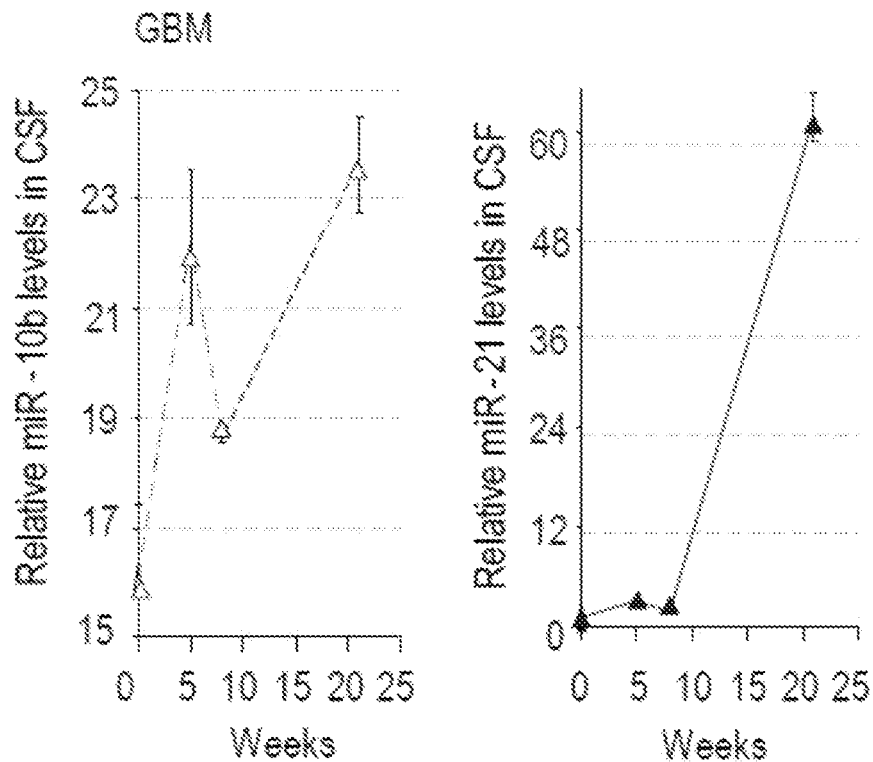
Figure 4B:
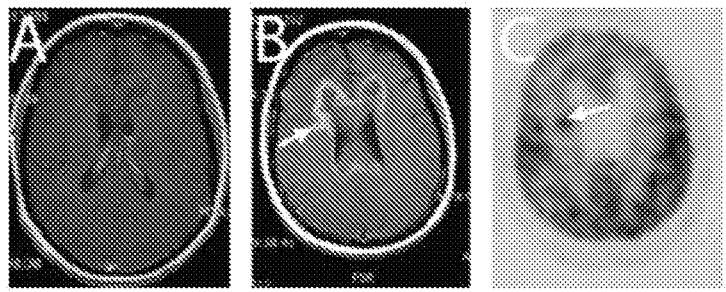
Figure 4C:
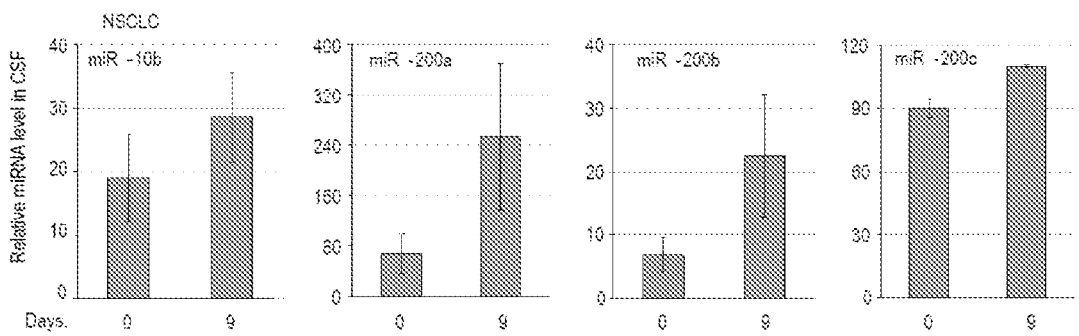
Figure 5A:
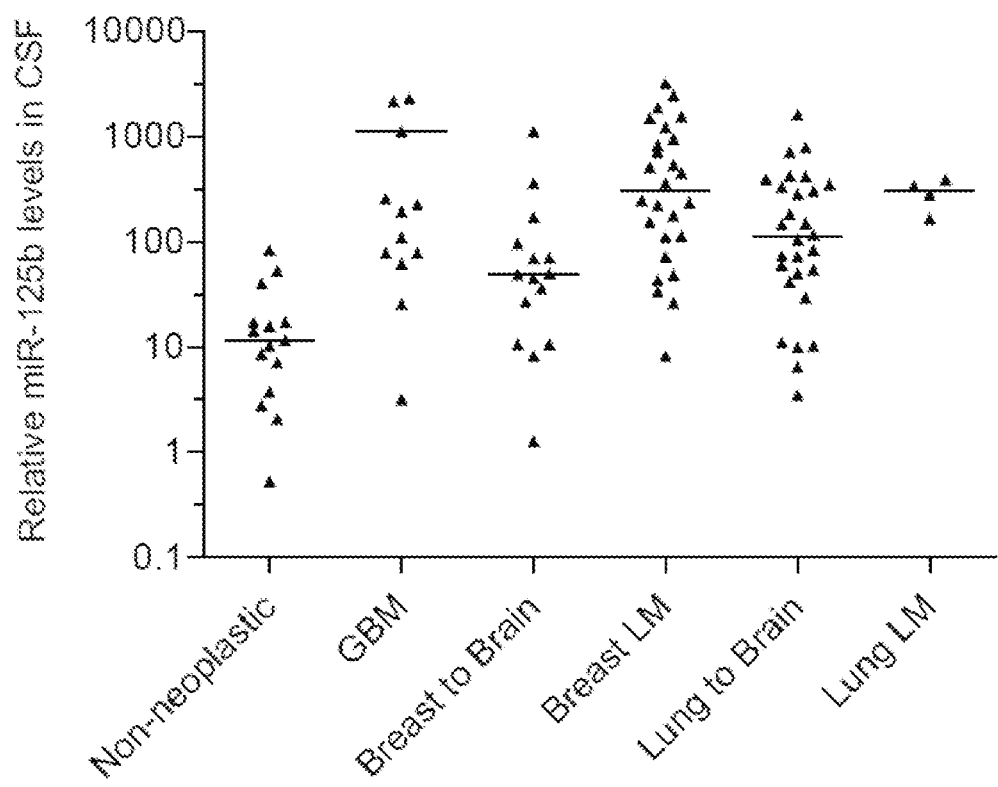
FIGS. 5A-G are graphs showing miR-NA levels in CSF of patients with GBM, metastatic brain cancers and non-neoplastic neurological conditions. miR-NA levels were determined in CSF samples by qRT-PCR and relative levels calculated by ΔCt method with expression at Ct=36 set as one unit.
Figure 5B:
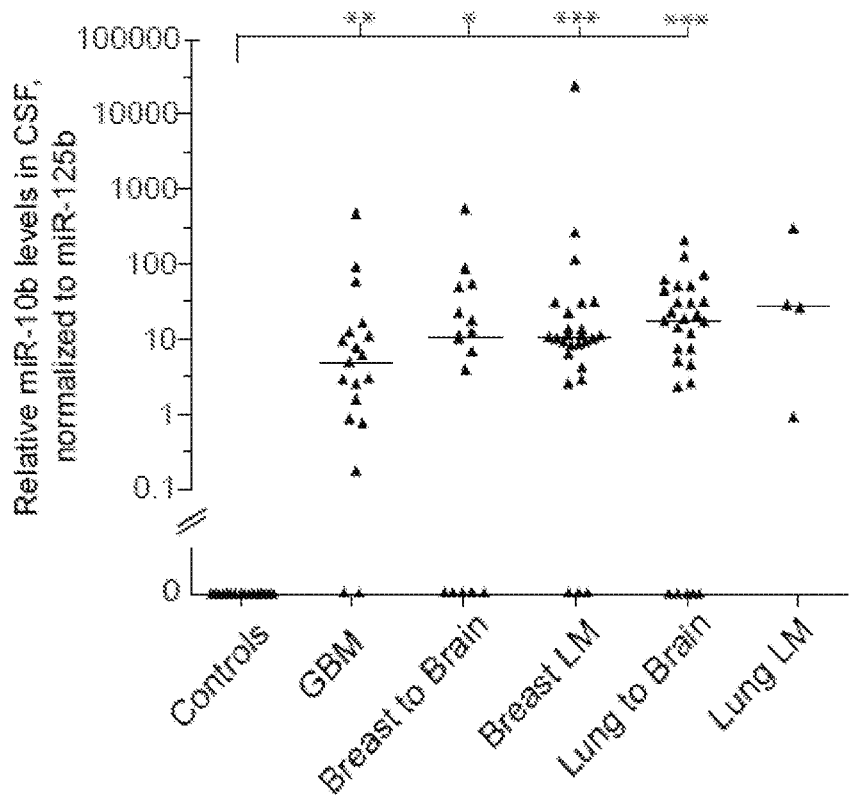
Figure 5C:
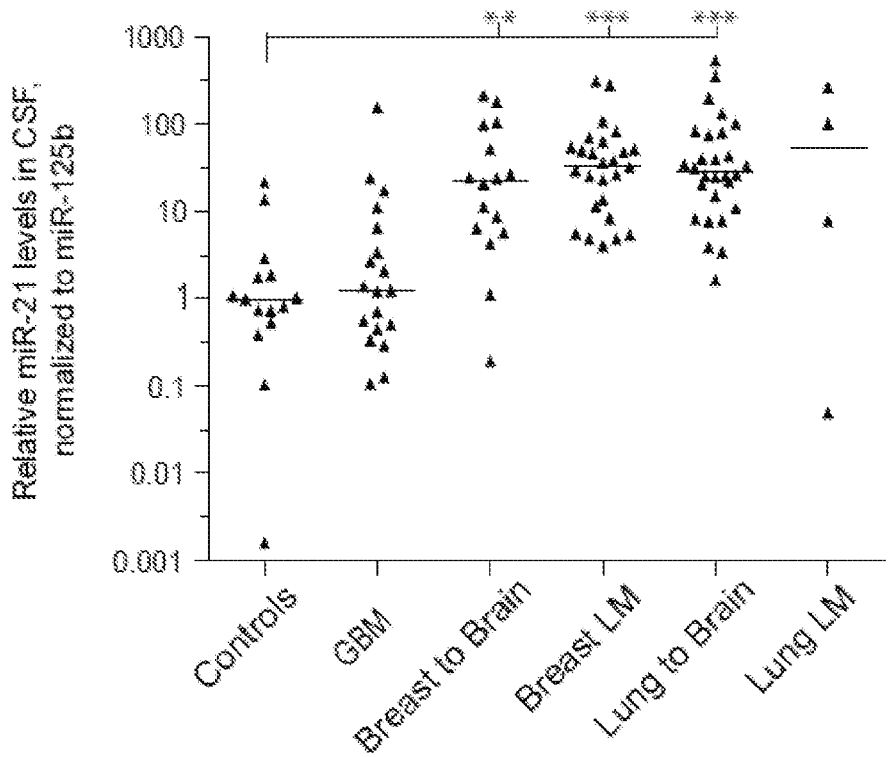
Figure 5D:
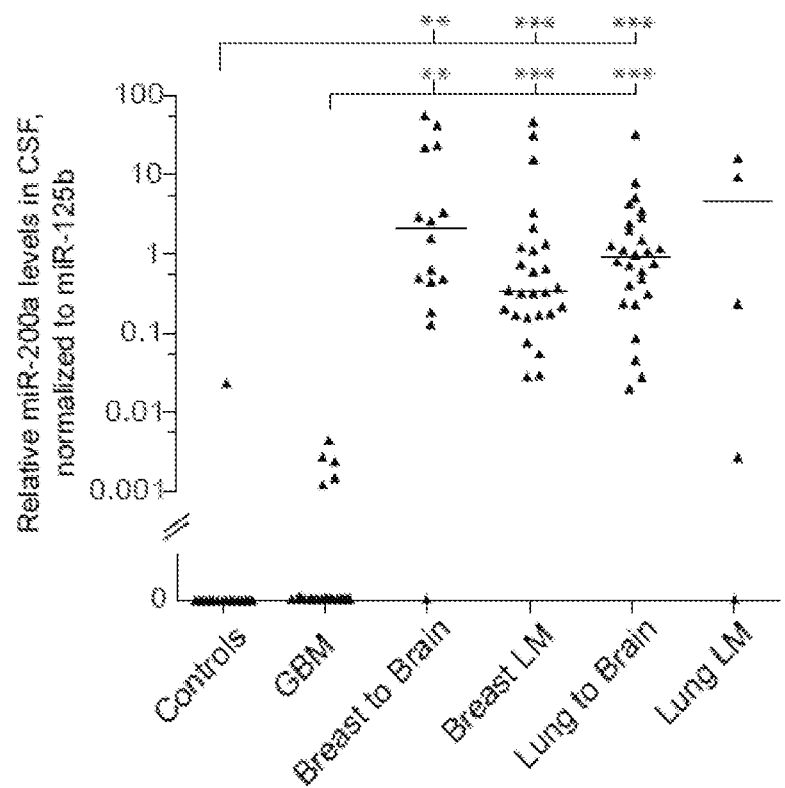
Figure 5E:
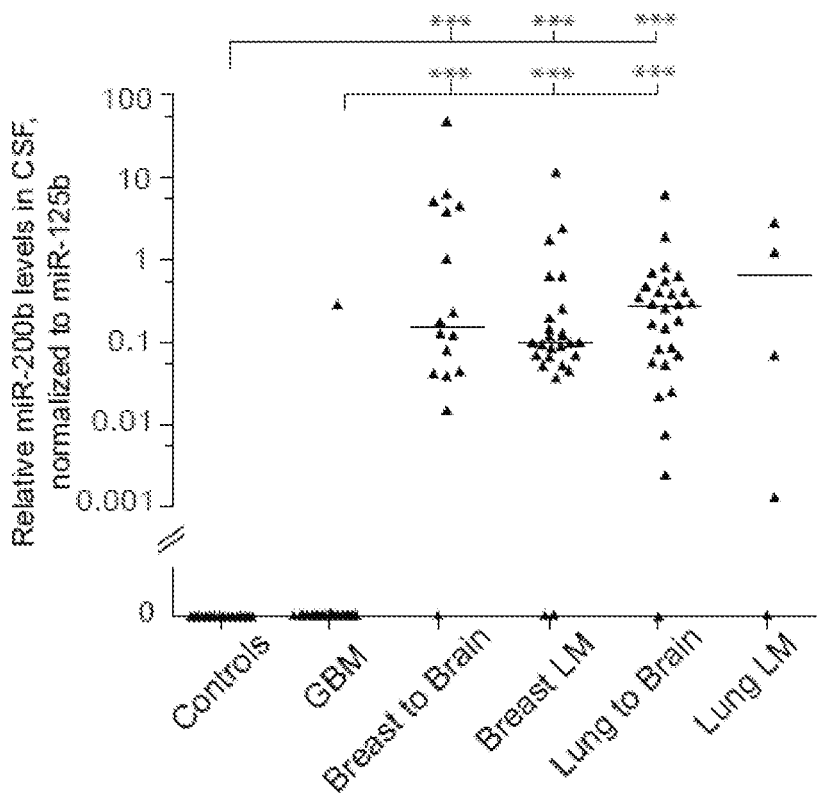
Figure 5F:
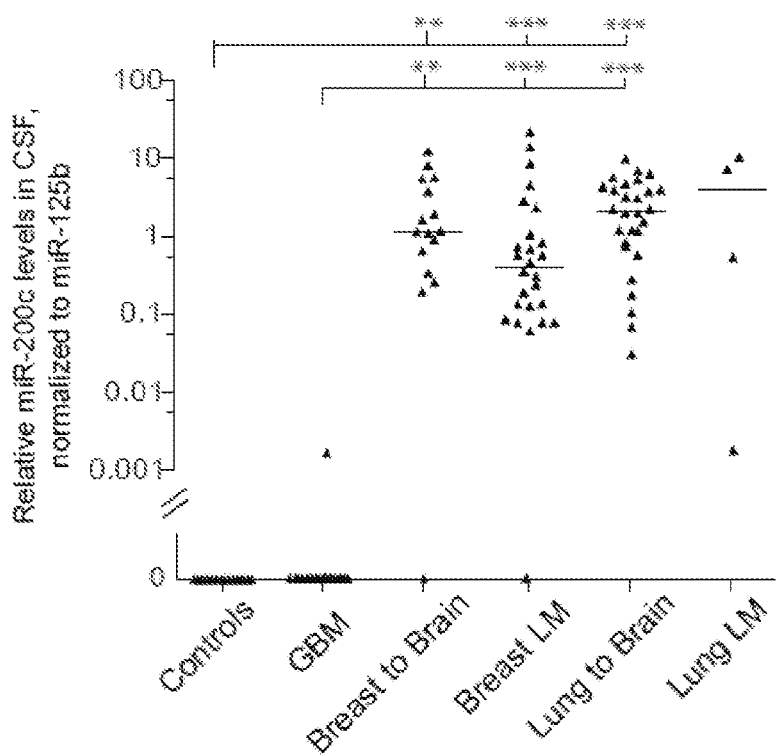
Figure 5G:
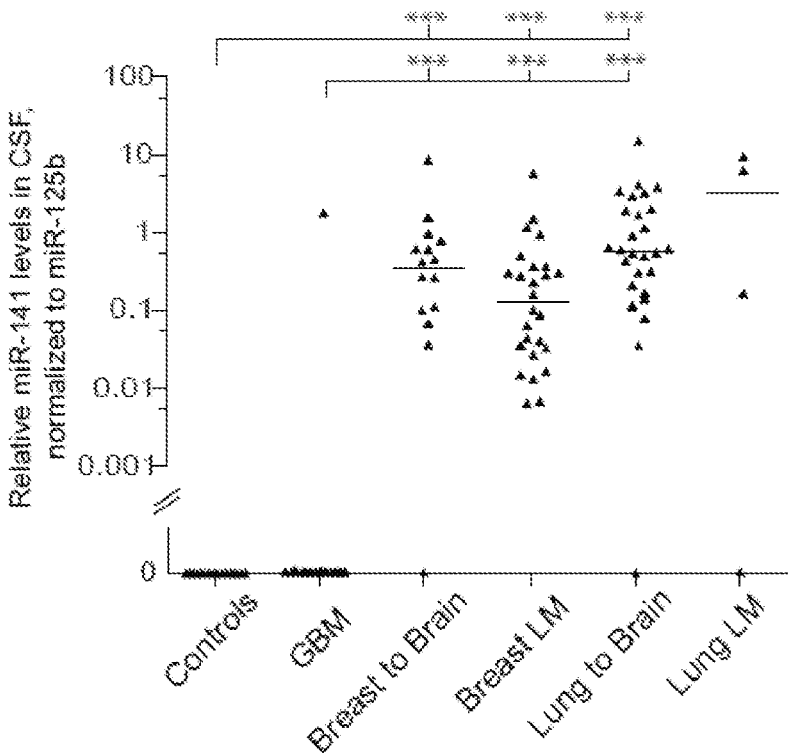

To further test whether the CSF levels of specific miRNAs reflect the disease status/activity and responsiveness to therapy, miRNA levels were determined in CSF of lung cancer and GBM patients longitudinally during course of erlotinib treatment. miRNA analysis was accompanied by MRI, CSF cytology, and clinical monitoring of the disease status. A NSCLC patient (patient A) developed parenchymal and leptomeningeal disease during course of treatment and medication adjustment (FIG. 4A). Erlotinib, an EGFR tyrosine kinase inhibitor, was given orally at the dose of 150 mg daily and increased at time of progression to 600 mg every 4 days and further to 900 mg (at 41 weeks) to achieve higher brain/CSF concentration[29], followed by a prolonged remission. The levels of both miR-10b and miR-200 members in CSF of this patient are consistent with the MRI results, rising during relapse and returning back to background levels after the increase of erlotinib dosage (significant drop by 45 weeks, FIG. 4A).

Patient B (FIG. 4B) had GBM in remission at the initial cytological CSF analysis and MRI that was interpreted as pseudoprogression. However, high levels of miR-10b, and significant elevation in miR-21 levels at later time indicated disease progression that was further confirmed by MRI, PET scan and repeat biopsy of new lesion. Patient C (FIG. 4C) had inadequate treatment due to functional status and rapidly progressed over a few weeks, which was reflected by an increase in levels of miR-200 family members.

Altogether, these data indicate for the first time that CSF miRNA levels may serve as biomarkers of brain cancer progression and response to therapy.

TABLE 3

| miRNA Ct values | 125b | 10b | 21 | 141 | 200a | 200b | 200c |
|---|---|---|---|---|---|---|---|
| GBM | 31.7864 | UD | 29.3547 | UD | UD | UD | 39.7125 |
| remission | 31.9339 | UD | 29.1258 | UD | UD | UD | 39.1993 |
| GBM | 33.5069 | UD | 32.0307 | UD | UD | UD | UD |
| remission | 33.8544 | UD | 32.6707 | UD | UD | UD | UD |
| GBM | 35.658 | UD | 34.5313 | UD | UD | UD | UD |
| remission | 35.5648 | UD | 36.6153 | UD | UD | UD | UD |
| NSCLC | 33.9462 | UD | 32.8533 | UD | UD | UD | UD |
| remission | 33.2768 | UD | 33.3858 | UD | UD | UD | UD |
| NSCLC | 28.28 | UD | 27.57 | UD | UD | UD | UD |
| remission | 28.28 | UD | 27.57 | UD | UD | UD | UD |
| NSCLC | 35.02 | UD | 31.35 | UD | UD | UD | UD |
| remission | 35.02 | UD | 31.35 | UD | UD | UD | UD |
| Breast carcinoma | 28.28 | 33.51 | 27.03 | UD | UD | UD | UD |
| remission | 28.28 | 33.51 | 27.03 | UD | UD | UD | UD |

REFERENCES

1. Filippini G, Falcone C, Boiardi A, et al. Prognostic factors for survival in 676 consecutive patients with newly diagnosed primary glioblastoma. Neuro Oncol. 2008; 10(1): 79-87.
2. Valadi H, Ekstrom K, Bossios A, et al. Exosome-mediated transfer of mRNAs and microRNAs is a novel mechanism of genetic exchange between cells. Nat Cell Biol. 2007; 9(6):654-659.
3. Skog J, Wurdinger T, van Rijn S, et al. Glioblastoma microvesicles transport RNA and proteins that promote tumour growth and provide diagnostic biomarkers. Nat Cell Biol. 2008; 10(12):1470-1476.
4. Chen X, Ba Y, Ma L, et al. Characterization of microRNAs in serum: a novel class of biomarkers for diagnosis of cancer and other diseases. Cell Res. 2008; 18(10):997-1006.
5. Lawrie C H, Gal S, Dunlop H M, et al. Detection of elevated levels of tumour-associated microRNAs in serum of patients with diffuse large B-cell lymphoma. Br J. Haematol. 2008; 141(5):672-675.
6. Gilad S, Meiri E, Yogev Y, et al. Serum microRNAs are promising novel biomarkers. PLoS One. 2008; 3(9):e3148.
7. Mitchell P S, Parkin R K, Kroh E M, et al. Circulating microRNAs as stable blood-based markers for cancer detection. Proc Natl Acad Sci USA. 2008; 105(30):10513-10518.
8. Cogswell J P, Ward J, Taylor I A, et al. Identification of miRNA changes in Alzheimer's disease brain and CSF yields putative biomarkers and insights into disease pathways. J Alzheimers Dis. 2008; 14(1):27-41.
9. Weber J A, Baxter D H, Zhang S, et al. The microRNA spectrum in 12 body fluids. Clin Chem. 56(11):1733-1741.
10. Baraniskin A, Kuhnhenn J, Schlegel U, et al. Identification of microRNAs in the cerebrospinal fluid as marker for primary diffuse large B-cell lymphoma of the central nervous system. Blood. 2011.
11. Birks D K, Barton V N, Donson A M, et al. Survey of MicroRNA expression in pediatric brain tumors. Pediatr Blood Cancer. 56(2):211-216.
12. Network CGAR. Comprehensive genomic characterization defines human glioblastoma genes and core pathways. Nature. 2008; 455(7216):1061-1068.
13. Nass D, Rosenwald S, Meiri E, et al. MiR-92b and miR-9/9*are specifically expressed in brain primary tumors and can be used to differentiate primary from metastatic brain tumors. Brain Pathol. 2009; 19(3):375-383.

14. Chan J A, Krichevsky A M, Kosik K S. MicroRNA-21 is an antiapoptotic factor in human glioblastoma cells. Cancer Res. 2005; 65(14):6029-6033.
15. Gabriely G, Yi M, Narayan R S, et al. Human glioma growth is controlled by microRNA-10b. Cancer Res. 2011; 71(10):3563-3572.
16. Gabriely G, Wurdinger T, Kesari S, et al. MicroRNA 21 promotes glioma invasion by targeting matrix metalloproteinase regulators. Mol Cell Biol. 2008; 28(17):5369-5380.
17. Sasayama T, Nishihara M, Kondoh T, et al. MicroRNA-10b is overexpressed in malignant glioma and associated with tumor invasive factors, uPAR and RhoC. Int J. Cancer. 2009; 125(6):1407-1413.
18. Baffa R, Fassan M, Volinia S, et al. MicroRNA expression profiling of human metastatic cancers identifies cancer gene targets. J. Pathol. 2009; 219(2):214-221.
19. Ma L, Teruya-Feldstein J, Weinberg R A. Tumour invasion and metastasis initiated by microRNA-10b in breast cancer. Nature. 2007; 449(7163):682-688.
20. Krichevsky A M, Gabriely G. miR-21: a small multifaceted RNA. J Cell Mol Med. 2009; 13(1):39-53.
21. Lu J, Getz G, Miska E A, et al. MicroRNA expression profiles classify human cancers. Nature. 2005; 435(7043): 834-838.
22. Liang Y, Ridzon D, Wong L, Chen C. Characterization of microRNA expression profiles in normal human tissues. BMC Genomics. 2007; 8:166.
23. Zhang C, Wang C, Chen X, et al. Expression profile of microRNAs in serum: a fingerprint for esophageal squamous cell carcinoma. Clin Chem. 56(12):1871-1879.
24. Volinia S, Calin G A, Liu C G, et al. A microRNA expression signature of human solid tumors defines cancer gene targets. Proc Natl Acad Sci USA. 2006; 103(7):2257-2261.
25. Heneghan H M, Miller N, Kelly R, et al. Systemic miRNA-195 differentiates breast cancer from other malignancies and is a potential biomarker for detecting noninvasive and early stage disease. Oncologist. 2010; 15(7): 673-682.
26. Zhang C, Li H R, Fan J B, et al. Profiling alternatively spliced mRNA isoforms for prostate cancer classification. BMC Bioinformatics. 2006; 7:202.
27. Murakami Y, Yasuda T, Saigo K, et al. Comprehensive analysis of microRNA expression patterns in hepatocellular carcinoma and non-tumorous tissues. Oncogene. 2006; 25(17):2537-2545.
28. Keller A, Leidinger P, Borries A, et al. miRNAs in lung cancer—studying complex fingerprints in patient's blood cells by microarray experiments. BMC Cancer. 2009; 9:353.
29. Jackman D M, Holmes A J, Lindeman N, et al. Response and resistance in a non-small-cell lung cancer patient with an epidermal growth factor receptor mutation and leptomeningeal metastases treated with high-dose gefitinib. J Clin Oncol. 2006; 24(27):4517-4520.
30. Schramedei K, Morbt N, Pfeifer G, et al. MicroRNA-21 targets tumor suppressor genes ANP32A and SMARCA4. Oncogene. 30(26):2975-2985.
31. Gaur A B, Holbeck S L, Colburn N H, Israel M A. Downregulation of Pdcd4 by mir-21 facilitates glioblastoma proliferation in vivo. Neuro Oncol. 13(6):580-590.
32. Korpal M, Kang Y. The emerging role of miR-200 family of microRNAs in epithelial-mesenchymal transition and cancer metastasis. RNA Biol. 2008; 5(3):115-119.
33. Baraniskin A, Kuhnhenn J, Schlegel U, et al. Identification of microRNAs in the cerebrospinal fluid as biomarker for the diagnosis of glioma. Neuro Oncol. 2011.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting or making a diagnosis between metastatic and primary brain tumors, the method comprising:
   determining, using real time polymerase chain reaction (RT-PCR) or an RNA expression assay, levels of miR-10b, miR-21, and miR-200 in a sample comprising cerebrospinal fluid (CSF) from a subject, and
   comparing the levels of miR-10b, miR-21, and miR-200 to reference levels of miR-10b, miR-21, and at least one miR-200 family member, and
   determining that the subject does not have a metastatic or primary brain tumor when the levels of all of miR200, miR-10b or miR-21 are below the reference levels;
   diagnosing a metastatic or primary brain tumor in a subject who has levels of miR-10b or miR-21 above the reference levels, and administering a treatment for a metastatic or primary brain tumor to the subject; and
   diagnosing a metastatic brain tumor when the levels of the miR-200 family member are above the reference level, and administering a treatment for metastatic brain cancer to a subject who has levels of the miR-200 family member above the reference level.

2. The method of claim 1, wherein the miR-200 family member is selected from the group consisting of miR-200a, miR-200b, and miR-200c.

3. A computer-implemented method of assigning a sample into a category, the method comprising:
   determining levels of miR-10b, miR-21, and at least one miR-200 family member, in a sample comprising cerebrospinal fluid (CSF) from a subject, to provide a subject dataset;
   downloading the subject dataset into a computer system having a memory, an output device, and a processor programmed for executing an algorithm, wherein the algorithm assigns the datasets into one of two categories using levels of miR-10b, miR-21, and at least one miR-200 family member;
   assigning the subject dataset into the first or second category using the programmed processor; and
   generating an output comprising a report indicating the assignment to the first or second category.

4. The method of claim 3, wherein the first category is presence of a primary brain tumor and the second category is presence of a metastatic brain tumor.

5. The method of claim 3, wherein the first category is presence of a primary brain tumor or a metastatic brain tumor, and the second category is absence of a primary brain tumor or a metastatic brain tumor.

6. The method of claim 3, wherein the algorithm is a linear algorithm or radial basis function.

7. The method of claim 3, wherein the algorithm is a linear algorithm comprising: (a*miR-125b)+(b*miR-10b)+(c*miR-21)+(d*miR-141)+(e*miR-200a)+(f*miR-200b)+(g*miR-200c)−h, wherein a-g are weights and h is a constant.

8. The method of claim 3, wherein the miR-200 family member is selected from the group consisting of miR-200a, miR-200b, miR-200c, miR-141, and miR-429.

9. A method of detecting or making a diagnosis between metastatic and primary brain tumors, the method comprising:

determining, using real time polymerase chain reaction (RT-PCR) or an RNA expression assay, levels of miR-10b, miR-21, and at least one miR-200 family member in a sample comprising cerebrospinal fluid (CSF) from a subject, and using a suitably programmed processor to apply a linear algorithm to the levels of miR-10b, miR-21, and miR-200 to classify the sample as (i) a primary brain tumor or (ii) a metastatic brain tumor, and diagnosing a metastatic brain tumor in a subject classified as having a metastatic brain tumor, and diagnosing a primary brain tumor in a subject classified as having a primary brain tumor.

10. The method of claim 9, comprising:

selecting a subject classified as having a metastatic brain tumor, and administering a treatment for metastatic brain cancer to the subject; or selecting a subject classified as having a metastatic or primary brain tumor, and administering a treatment for primary brain cancer to the subject.

11. The method of claim 9, comprising determining levels of miR-125b, miR-10b, miR-21, miR-141, miR-200a, miR-200b, and miR-200c, wherein the linear algorithm comprises: (a*miR-125b)+(b*miR-10b)+(c*miR-21)+(d*miR-141)+(e*miR-200a)+(f*miR-200b)+(g*miR-200c)−h, wherein a-g are weights and h is a constant.

* * * * *